United States Patent [19]

Kraus et al.

[11] Patent Number: 5,324,263
[45] Date of Patent: Jun. 28, 1994

[54] LOW PROFILE HIGH PERFORMANCE INTERVENTIONAL CATHETERS

[75] Inventors: Jeff L. Kraus, San Jose, Calif.; Robert D. Lashinski, St. Michael, Minn.

[73] Assignee: Danforth Biomedical, Inc., Menlo Park, Calif.

[21] Appl. No.: 41,436

[22] Filed: Mar. 31, 1993

Related U.S. Application Data

[60] Division of Ser. No. 730,240, Jul. 15, 1991, Pat. No. 5,256,144, which is a continuation-in-part of Ser. No. 430,702, Nov. 2, 1989, abandoned.

[51] Int. Cl.⁵ .............................................. A61M 25/00
[52] U.S. Cl. ...................................... 604/96; 604/171; 606/194; 606/193
[58] Field of Search .................. 604/95, 96, 101, 164, 604/280, 282, 165, 171; 128/657, 772, 344; 606/191-194

[56] References Cited

U.S. PATENT DOCUMENTS

| Re. 33,166 | 2/1990 | Samson | 606/194 |
|---|---|---|---|
| 4,195,637 | 4/1980 | Grüntzig et al. | 128/348 |
| 4,229,226 | 11/1981 | Banka | 128/344 |
| 4,323,071 | 4/1982 | Simpson et al. | 128/343 |
| 4,448,195 | 5/1984 | Le Veen et al. | 128/344 |
| 4,473,067 | 9/1984 | Schiff | 128/1 D |
| 4,573,470 | 3/1986 | Samson et al. | 128/344 |
| 4,582,181 | 4/1986 | Samson | 128/348.1 |
| 4,616,653 | 10/1986 | Samson et al. | 128/344 |
| 4,638,805 | 1/1987 | Powell | 128/344 |
| 4,641,654 | 2/1987 | Samson et al. | 128/344 |
| 4,664,113 | 5/1987 | Frisble et al. | 128/344 |
| 4,715,378 | 12/1987 | Pope, Jr. et al. | 128/344 |
| 4,723,936 | 2/1988 | Buchbinder et al. | 604/95 |
| 4,726,374 | 2/1988 | Bales et al. | 128/344 |
| 4,771,778 | 9/1988 | Mar | 128/344 |
| 4,790,315 | 12/1988 | Mueller, Jr. et al. | 128/344 |
| 4,793,350 | 12/1988 | Mar et al. | 128/344 |
| 4,808,164 | 2/1989 | Hess | 604/95 |
| 4,811,737 | 3/1989 | Rydell | 128/344 |
| 4,821,722 | 4/1989 | Miller et al. | 128/344 |
| 4,838,268 | 6/1989 | Keith et al. | 128/344 |
| 4,846,174 | 7/1989 | Willard et al. | 128/344 |
| 4,875,481 | 10/1989 | Higgins | 128/344 |
| 4,892,519 | 1/1990 | Songer et al. | 604/96 |
| 4,896,670 | 1/1990 | Crittenden | 606/194 |
| 4,906,241 | 3/1990 | Noddin et al. | 606/194 |
| 4,917,088 | 4/1990 | Crittenden | 606/194 |
| 4,927,413 | 5/1990 | Hess | 604/95 |
| 4,943,278 | 7/1990 | Euteneuer et al. | 604/96 |
| 4,955,384 | 9/1990 | Taylor et al. | 128/657 |
| 4,990,139 | 2/1991 | Jang | 604/101 |
| 5,032,113 | 7/1991 | Burns | 604/96 |
| 5,035,705 | 7/1991 | Burns | 606/194 |
| 5,158,548 | 10/1992 | Lau et al. | 604/96 |
| 5,160,321 | 11/1992 | Sahota | 604/96 |
| 5,255,690 | 10/1993 | Keith et al. | 128/772 |

FOREIGN PATENT DOCUMENTS

| 0279959A1 | 12/1987 | European Pat. Off. . |
|---|---|---|
| 0374859A1 | 12/1989 | European Pat. Off. . |
| 0376132A1 | 12/1989 | European Pat. Off. . |
| 0397038A1 | 5/1990 | European Pat. Off. . |
| 0398676A1 | 5/1990 | European Pat. Off. . |
| WO90/07909 | 1/1990 | PCT Int'l Appl. . |

OTHER PUBLICATIONS

Instruction Manual for Datascope ® Integra Dilatation Catheter, Publication No. 0900-04-0010 (A), Rev. Nov. 7, 1989, Datascope Corporation, 580 Winters Ave., Paramus, N.J. 07653-0005.

*Primary Examiner*—John D. Yasko
*Attorney, Agent, or Firm*—Townsend and Townsend Khourie and Crew

[57] ABSTRACT

A seal for a medical device such as a catheter is formed between two parts of the device which are capable of movement relative to each other, either axially, rotationally or both. The seal is formed by opposing sealing surfaces on each of the two parts, the surfaces being sufficiently smooth and of sufficiently close proximity that liquids having viscosities on the order of those normally used in catheters will not pass between the surfaces due to such effects as surface tension and friction. In certain embodiments, the surfaces are arranged to permit liquid to pass at a controlled rate for purposes of perfusion when desired, or the surfaces can be moved relative to one another to achieve this capability.

6 Claims, 23 Drawing Sheets

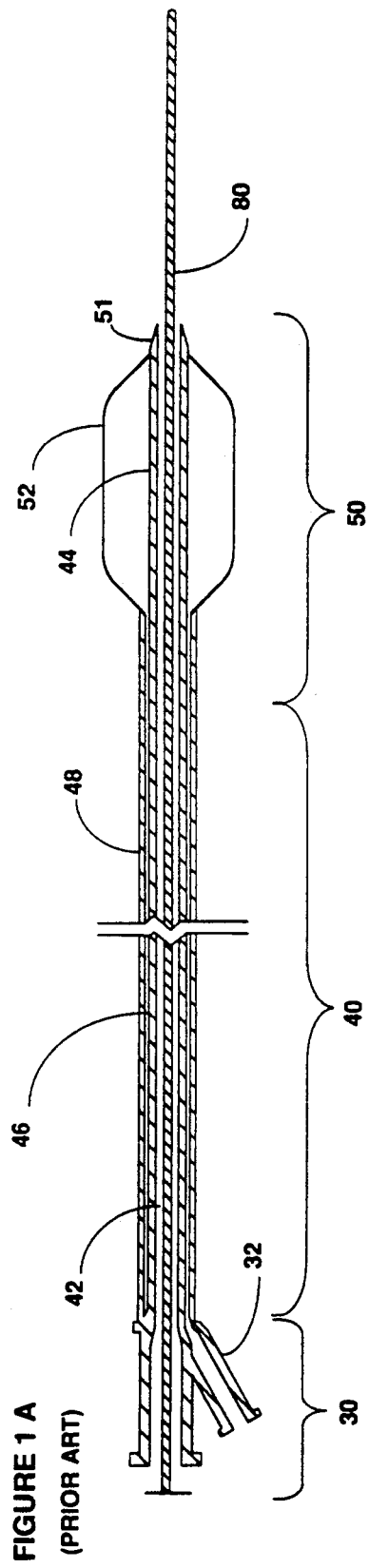
FIGURE 1 A
(PRIOR ART)
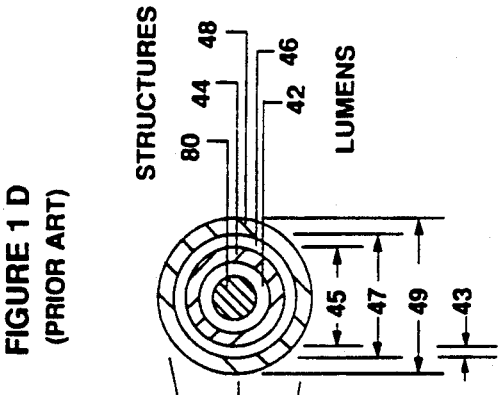
FIGURE 1 D
(PRIOR ART)
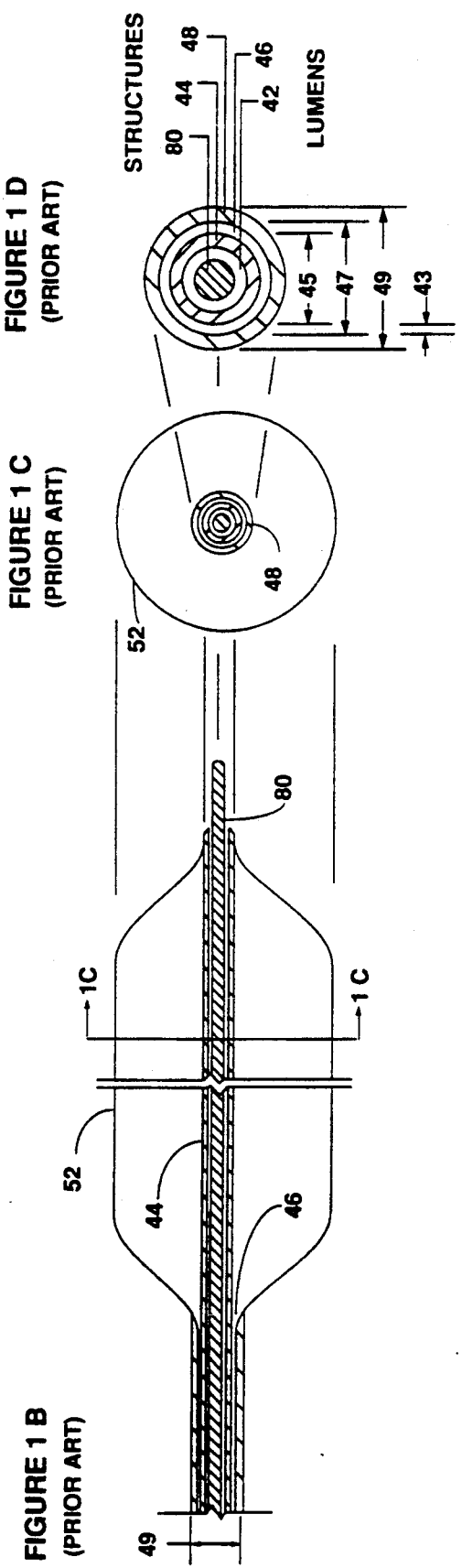
FIGURE 1 C
(PRIOR ART)
FIGURE 1 B
(PRIOR ART)

FIGURE 2 A
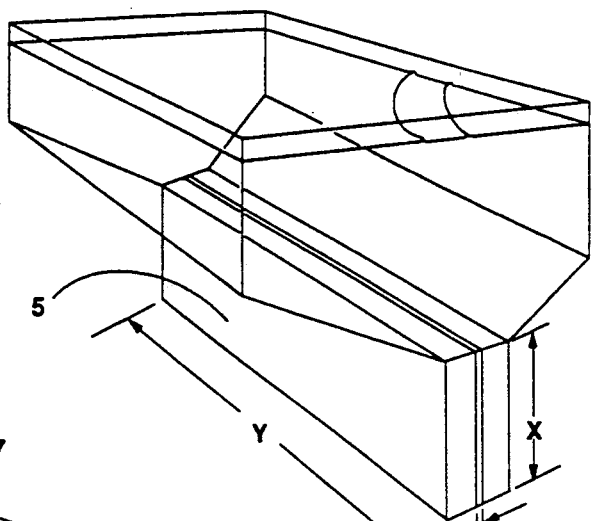
FIGURE 2 B
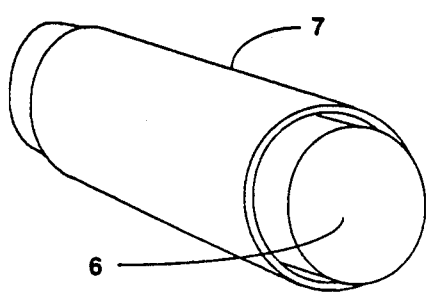
FIGURE 2 C
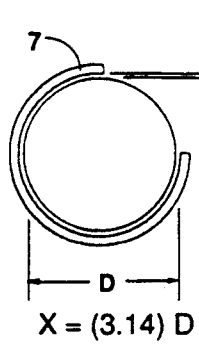
$X = (3.14) D$
FIGURE 2 D
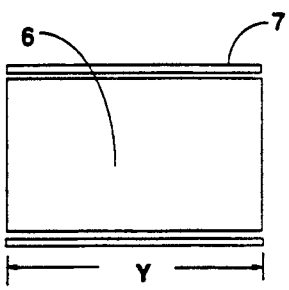
FIGURE 2 E  FIGURE 2 F
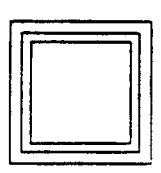 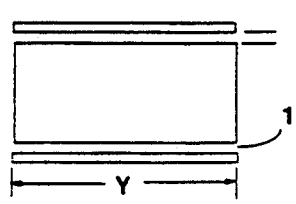
FIGURE 2 G  FIGURE 2 H
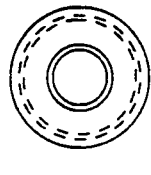 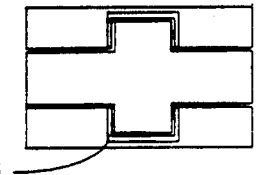

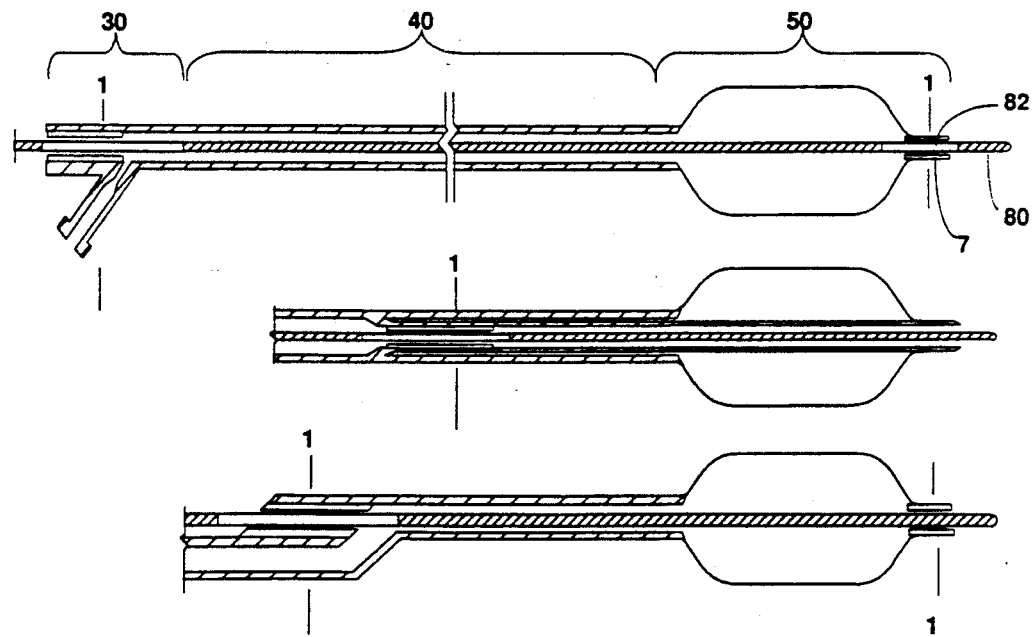

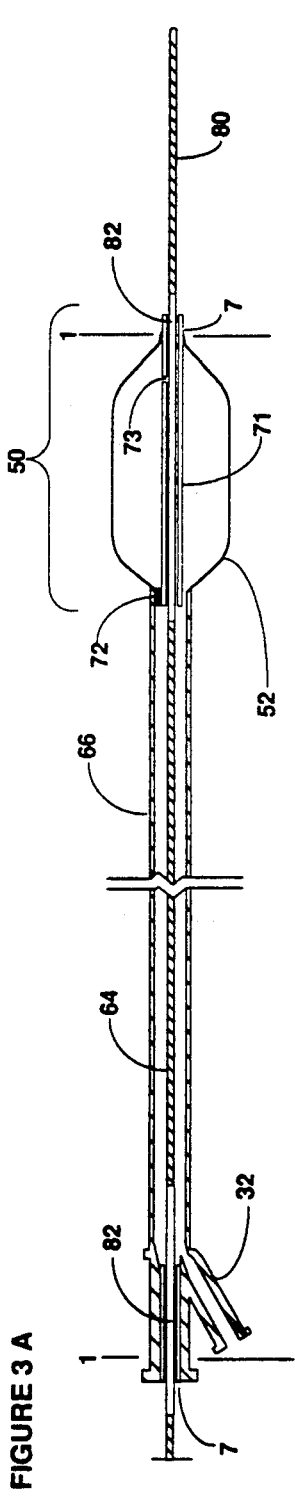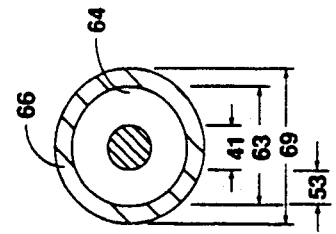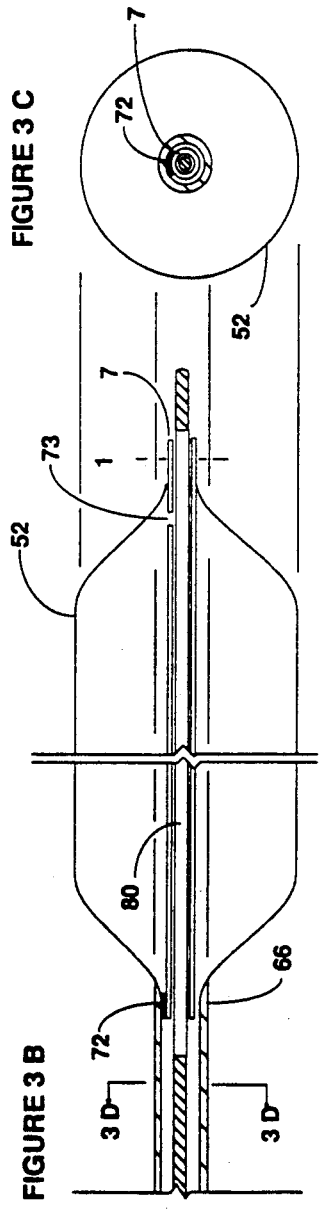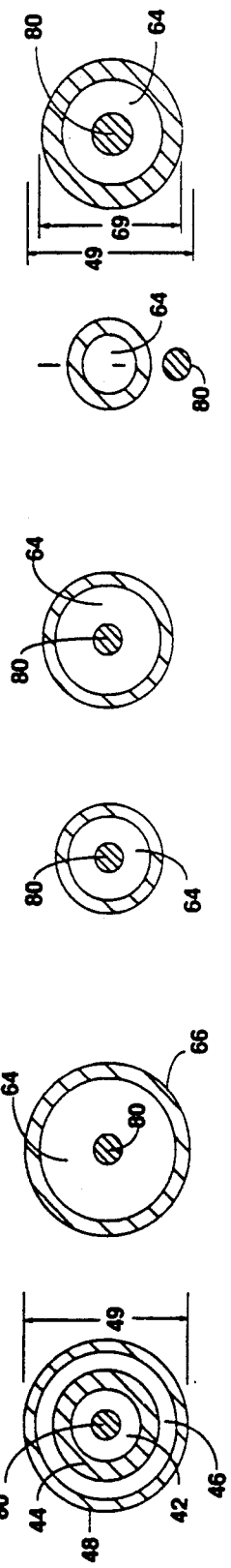

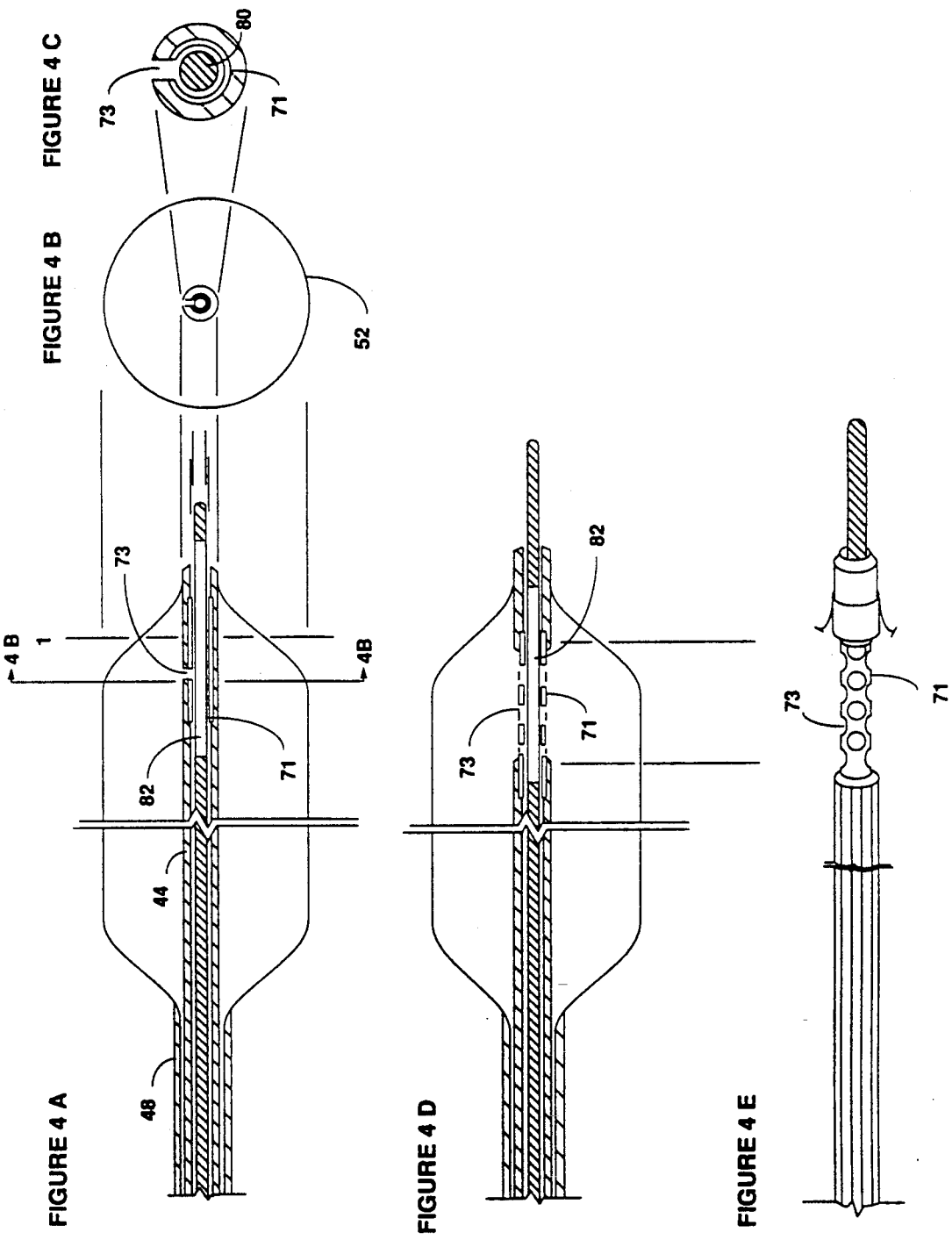

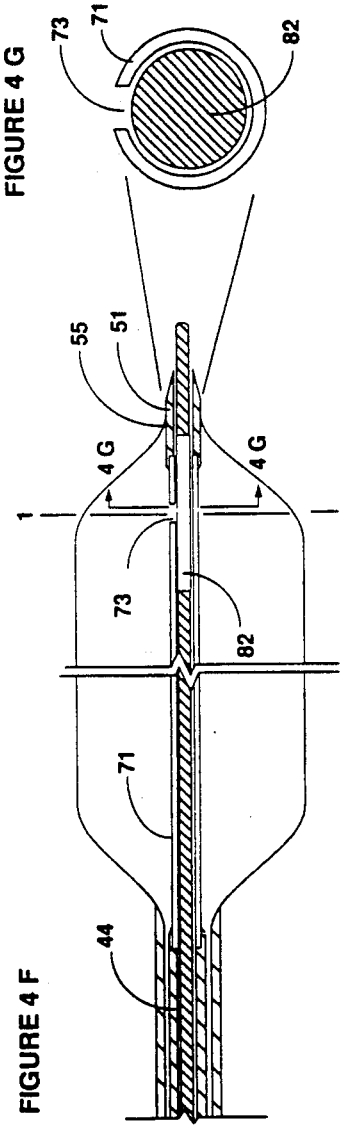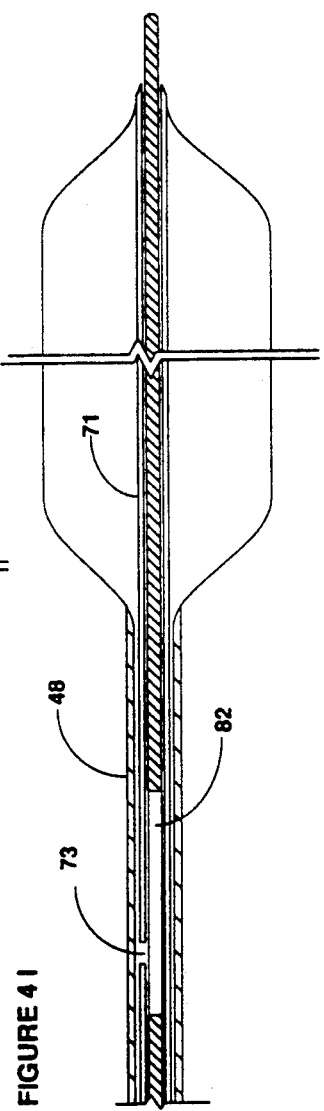

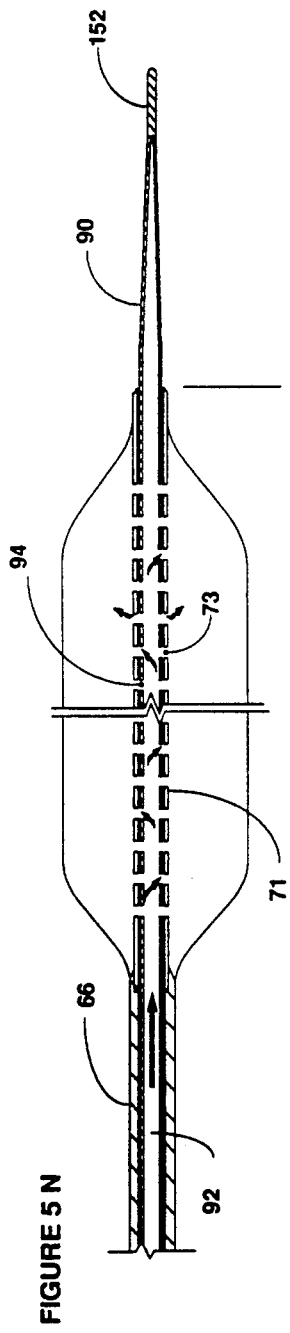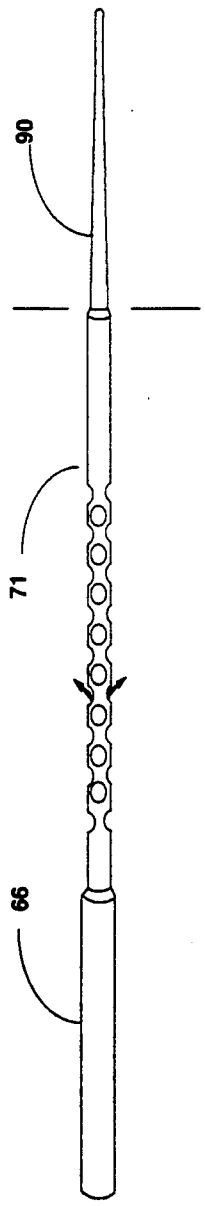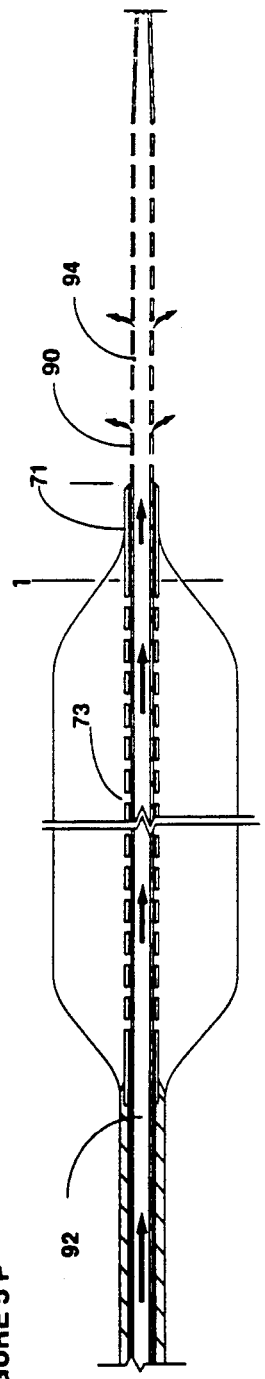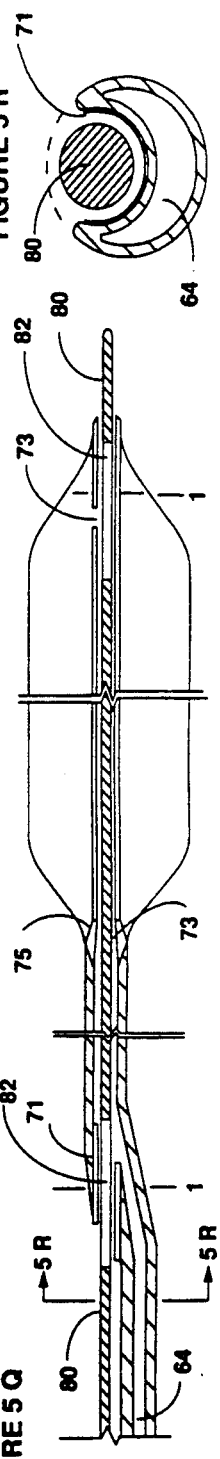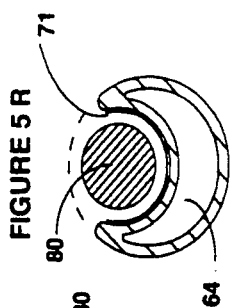
FIGURE 5 N
FIGURE 5 O
FIGURE 5 P
FIGURE 5 Q
FIGURE 5 R

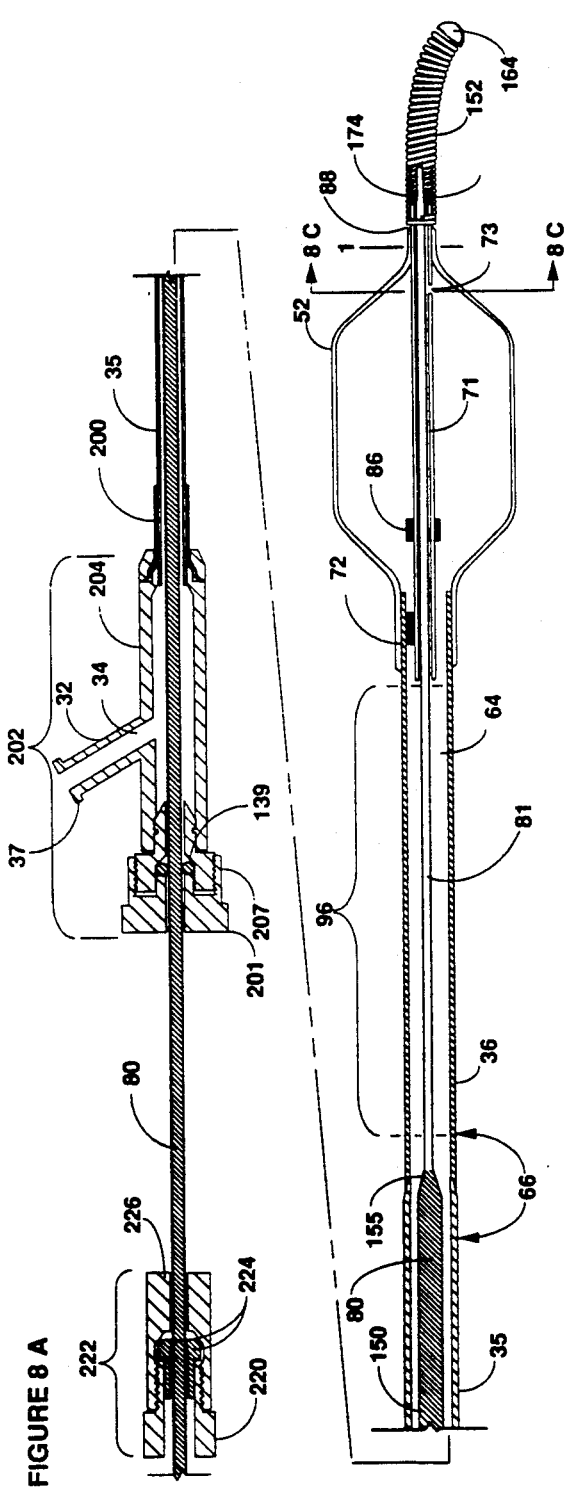
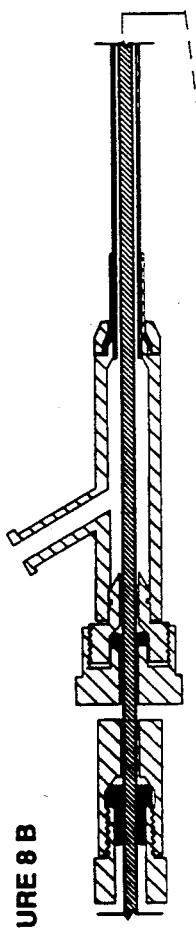
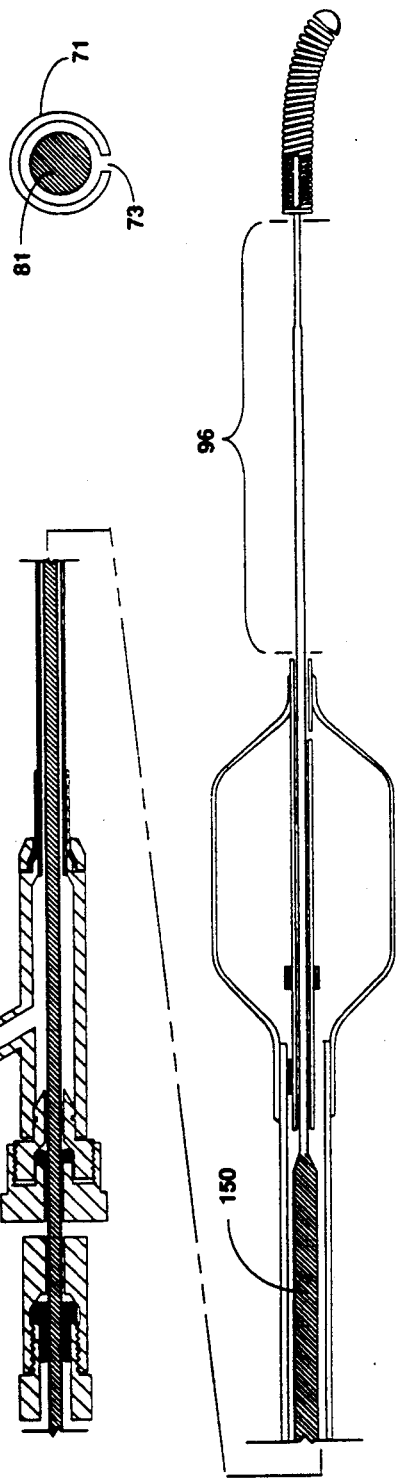

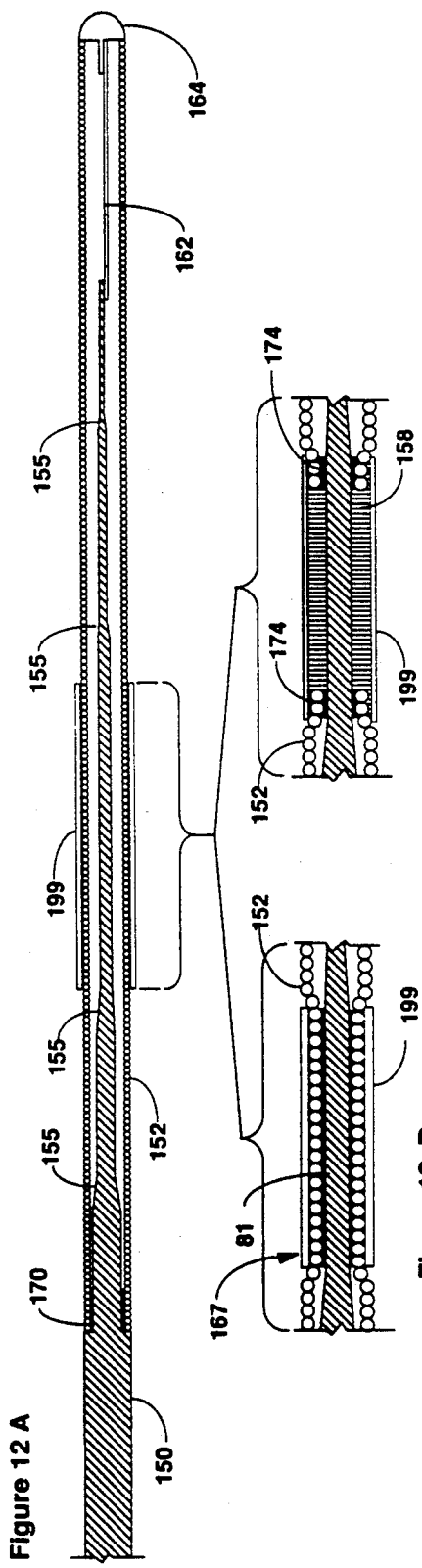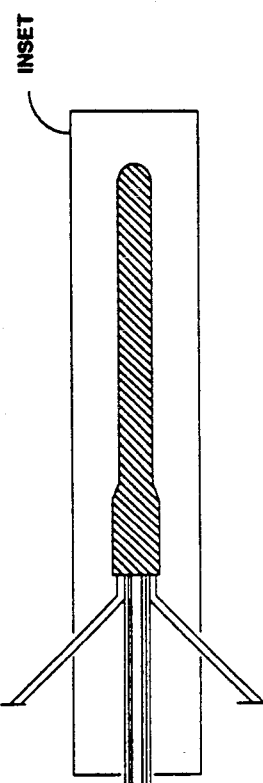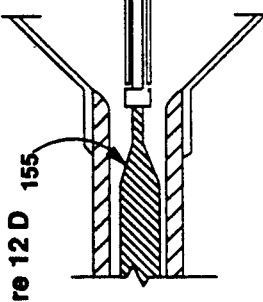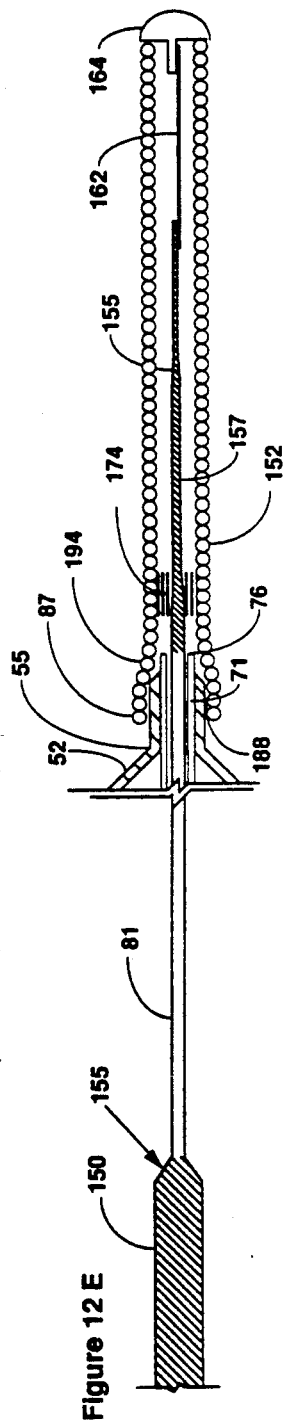
Figure 12 A
Figure 12 B
Figure 12 C
Figure 12 D
Figure 12 E

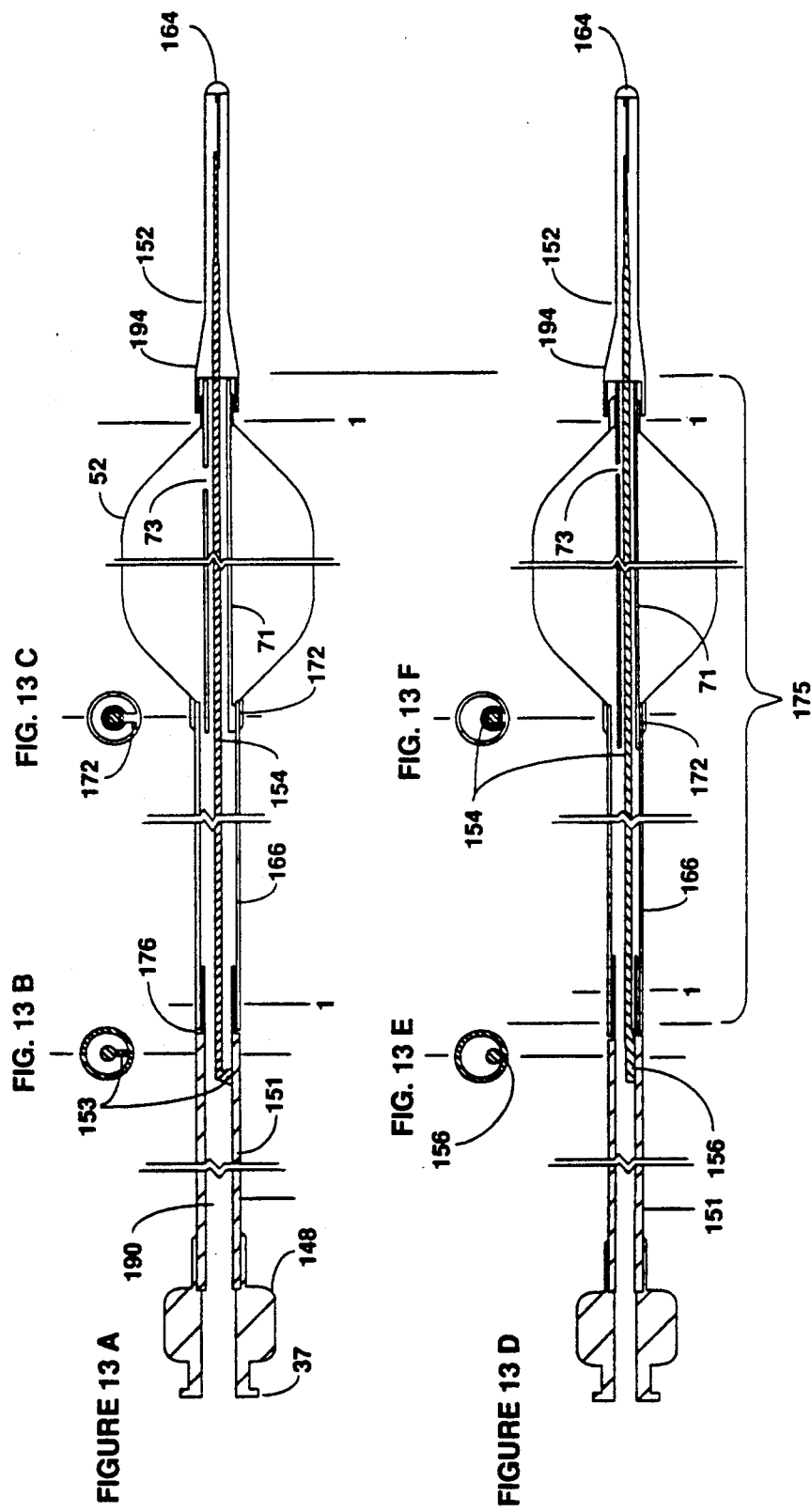

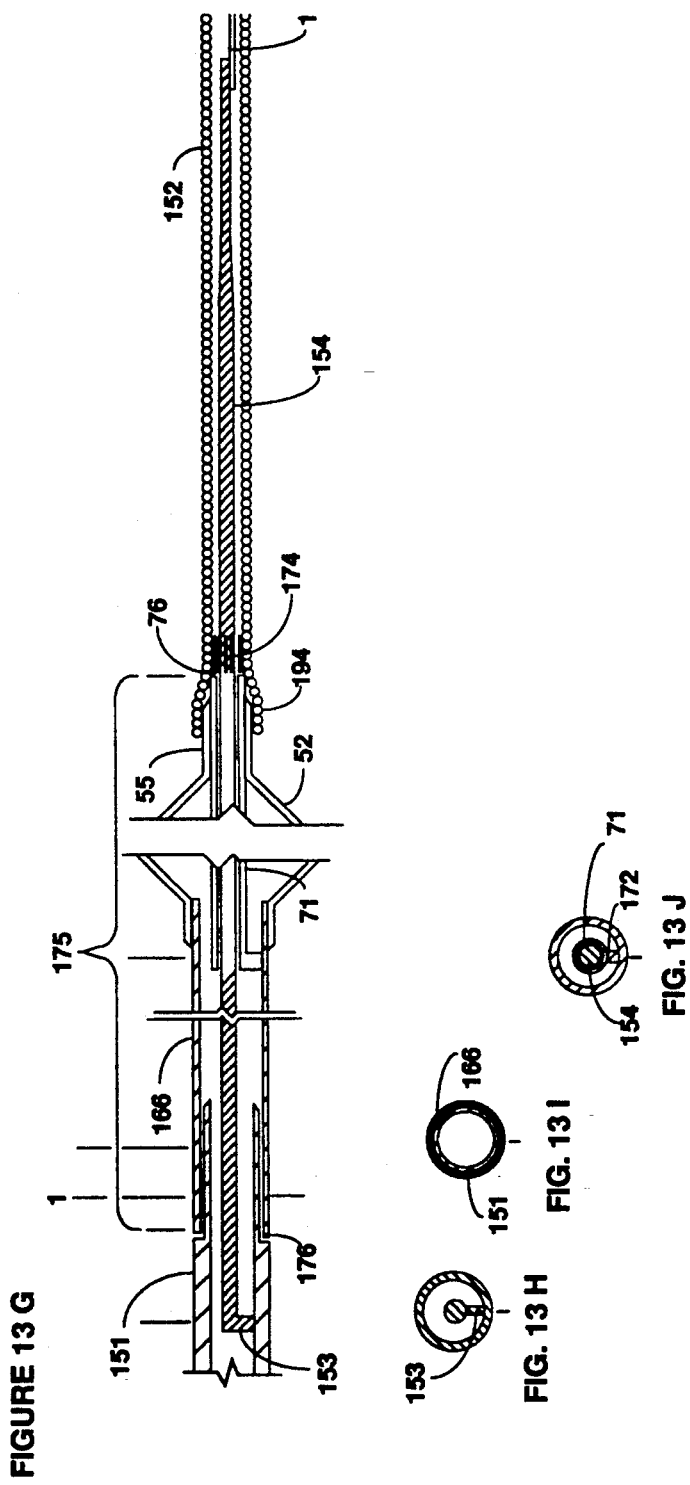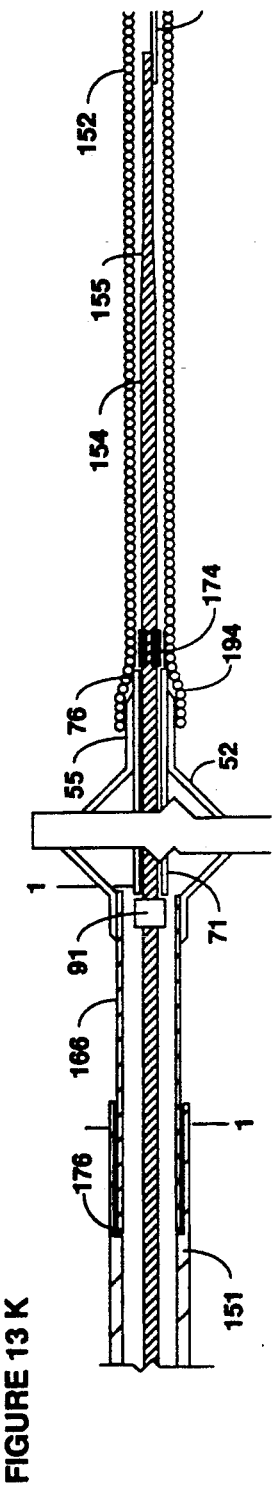

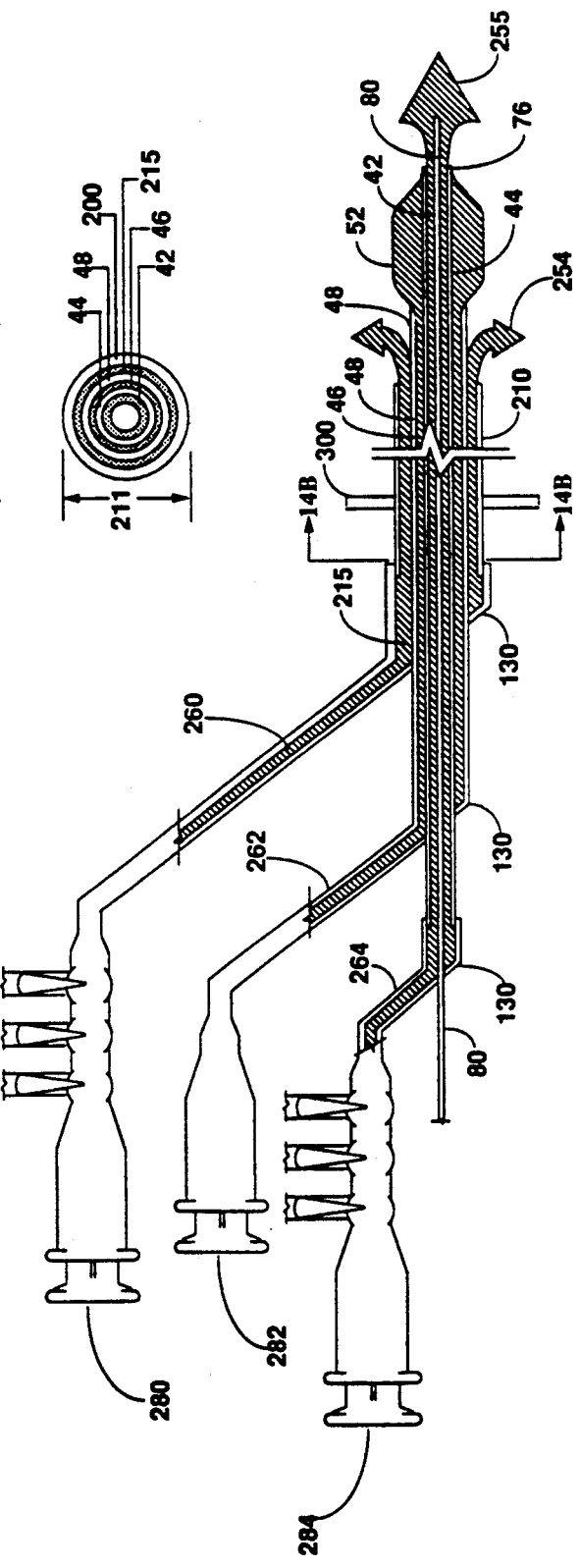

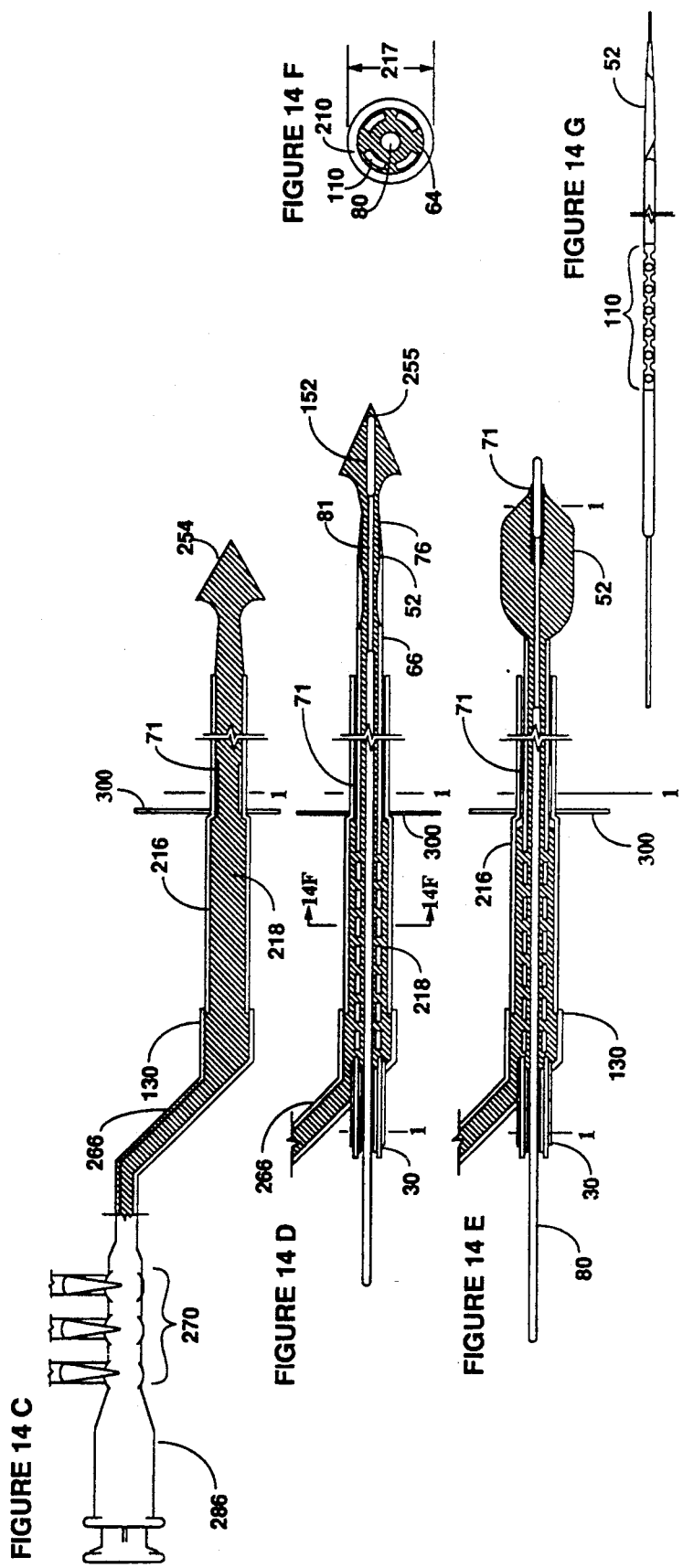

LOW PROFILE HIGH PERFORMANCE
INTERVENTIONAL CATHETERS

CROSS REFERENCE TO RELATED APPLICATION

This application is a division of pending application Ser. No. 07/730,240, filed Jul. 15, 1991, now U.S. Pat. No. 5,256,144 which is, in turn, a continuation-in-part of application Ser. No. 07/430,702, filed Nov. 2, 1989, now abandoned.

BACKGROUND OF THE INVENTION

This invention relates to catheters and catheter systems. In particular, this invention relates to seals in catheters and especially to seals in angioplasty dilatation balloon catheters and catheter systems.

Catheter Profile Considerations

Angioplasty has become a well accepted technique for the treatment of atherosclerotic cardiovascular disease. The performance-of this procedure requires the use of guidewire-directed dilatation balloon catheter systems. Considerable effort has been directed toward the development of these systems with progressively lower cross-sectional shaft and "crossing" profiles. Herein, the "crossing profile" of a particular angioplasty catheter refers to the cross-sectional profile of the balloon when deflated, while "shaft profile" refers to the dimensions of the cross-sectional profile of the catheter shaft communicating with the balloon. Smaller or "lower profile" catheters provide several advantages. They provoke less trauma during introduction within the vascular system. Catheters with lower "crossing profiles" require less effort to manipulate across severe obstructions than devices of larger crossing profile. Catheters with lower shaft profiles create less impairment to the surrounding flow of intra-vascular fluid, including blood, medications and contrast medium. Thus, these catheters: (1) provoke less intra-operative ischemia, (2) permit the delivery of blood, medications and blood substitutes within the vessel containing the catheter with superior flow rates and (3) permit the performance of intra-operative angiography with superior resolution, relative to comparable devices of larger cross-sectional shaft profile.

The resolution of conventional angiography is directly related to the rate of contrast injection into the vascular system. The rate of contrast injection is directly related to the cross-sectional area of the channel used to convey the contrast media into the intravascular system. During an angioplasty procedure, the cross-sectional area of this channel is effectively the cross-sectional area of the lumen of the guiding catheter less the cross-sectional area of the shaft of the dilatation balloon catheter contained therein. Thus, dilatation balloon catheters with lower cross-sectional shaft profiles enable the delivery of contrast medium within the vessels containing these devices with superior flow rates and thereby permit the performance of intra-operative angiography with superior angiographic resolution, relative to dilatation balloon catheters with larger shaft profiles.

In summary, dilatation balloon catheter systems with lower crossing and cross-sectional shaft profiles are easier and safer to use in many respects relative to their larger profile counterparts. Hence, considerable effort has been devoted to the development of progressively lower profile angioplasty catheter systems.

Much of the progress that has been achieved to date in the development of lower profile angioplasty dilatation balloon catheter systems, and particularly "over-the-wire" angioplasty catheter systems, has resulted from miniaturization. State-of-the-art plastics allow manufacture of the shaft and balloon components of these devices with thinner walls than previously possible. Other new technologies allow the construction of these devices with smaller caliber channels. Unfortunately, the practice of miniaturization provides diminishing returns. As will be described below, miniaturization adversely affects the pushability, hydraulic performance, steerability and trackability of angioplasty catheter systems.

To appreciate the relationship between the structure of angioplasty dilatation balloon catheters and the fundamental performance features influencing their clinical utility, conventional over-the-wire and non-over-the-wire angioplasty catheter systems are discussed below.

Prior Art Over-the-Wire Angioplasty Balloon catheters

FIGS. 1A-1F illustrate the structural features common to over-the-wire dilatation balloon catheter systems currently marketed worldwide, for example, as described in U.S. Pat. No. 4,323,071. Although alternative designs exist for the construction of multi-lumen dilatation balloon catheters, it should be recognized that the fundamental features of virtually all prior art over-the-wire catheters are similar. For the purpose of simplicity, we will confine our remarks concerning over-the-wire catheters to the catheter configuration depicted in FIGS. 1A-1F, with the understanding that these remarks apply to virtually all prior art over-the-wire devices, regardless of configuration.

The shaft 40 of the catheter shown in FIG. 1A contains two separate lumens 42, 46. Lumen 42 accommodates guidewire 80 while lumen 46 transmits fluid and hydraulic pressure along the length of the catheter. (Occasionally, over-the-wire catheters are constructed with three shaft lumens, with the third functioning as an air vent for the balloon.) The proximal end 30 of the catheter has an adapter 32 to interface with a source of hydraulic pressure, while the distal end 50 includes a balloon 52 for dilation of the artery or other vessel.

The pushability (or column strength) of an angioplasty system varies as a function of the compliance of the supporting element. Typically, over-the-wire systems rely upon the catheter shaft for column support whereas non-over-the-wire systems rely upon the guidewire for this support. The pushability of an over-the-wire system varies as a function of the rigidity and thickness of the material used in the walls of the catheter shaft. For the same material of construction, catheters having thinner shaft walls are less pushable, and thus more prone to axial compression, particularly during introduction across critical lesions. Accordingly, reducing the shaft wall thickness to reduce the shaft profile, without substituting a more rigid material, adversely affects the pushability of these systems and thus the clinical utility of these devices in the treatment of high grade lesions. Although this disadvantage has been partially offset by the use of increasingly rigid plastics for the shaft walls, increasing rigidity is only beneficial to a limited extent.

The hydraulic performance, or rate of inflation and deflation of the balloon, is related to the cross-sectional area of the hydraulic channel 46 that communicates with the balloon 52 to convey hydraulic pressure along the length of the catheter, and to the viscosity of the hydraulic medium used to transmit the hydraulic pressure. Catheters with smaller hydraulic channels have longer inflation/deflation times. Importantly, the balloon inflation/deflation rate influences the safety of the device and specifically its propensity to provoke ischemia. This arises because partial balloon inflation compromises blood flow, but accomplishes no therapeutic benefit. Balloons are always partially inflated during inflation and deflation. Reducing the cross-sectional area of the hydraulic channel to reduce the shaft profile of an over-the-wire angioplasty device adversely affects the hydraulic performance, and hence degrades the safety of the device.

The steerability, or directional control, of an angioplasty catheter system varies directly as a function of the profile of the guidewire mandrel and inversely as a function of the friction that develops in response to rotation of the guidewire relative to the catheter. The amount of friction that develops in this circumstance varies as a function of: (1) the normal force between the catheter and guidewire during inter-component rotation and (2) the coefficient of friction of the catheter-guidewire interface. The magnitude of the catheter-guidewire contact surface area varies inversely as a function of the catheter-guidewire clearance. Reducing the profile of the guidewire mandrel or reducing the catheter-guidewire clearance, with the aim to reduce the shaft profile, inevitably compromises the steerability of the composite system.

The trackability of a catheter-guidewire system, or the ease with which the catheter component can be advanced over the guidewire, varies as a function of the flexibility of the distal aspect of the catheter and the magnitude of linear resistance that develops between these system components during coaxial movement of one component relative to the other. The linear resistance that develops in this circumstance varies as a function of the magnitude of the contact surface area between the catheter and guidewire and the coefficient of friction of the catheter-guidewire interface. Reducing the catheter-guidewire clearance, with the aim to reduce the shaft profile, increases the catheter-guidewire contact surface area and thus compromises the trackability of the system.

To summarize, it becomes evident that there is a lower limit to the shaft profile that can be achieved in the construction of clinically acceptable over-the-wire catheters of conventional design. Further reduction of the profile of the catheter shafts of prior art over-the-wire catheter systems is limited by the factors discussed above. In particular further miniaturization of the shaft is limited by the need to:

(1) maintain the profile of the guidewire mandrel large enough to provide clinically acceptable steerability,
(2) maintain the clearance between the catheter and guidewire components sufficient to provide clinically acceptable steerability and trackability,
(3) maintain the profile of the hydraulic channel sufficient to provide clinically acceptable hydraulic performance,
(4) maintain the thickness of the shaft walls sufficient to provide clinically acceptable pushability, pressure tolerance and structural integrity, and
(5) maintain the flexibility of the distal aspect of the catheter shaft sufficient to provide clinically acceptable trackability.

Similar considerations apply to the progress that can be expected in further reducing the crossing profiles of over-the-wire systems of the prior art. Reducing the crossing profile of an over-the-wire system is limited by the need to:

(1) maintain the proximal profile of the guidewire mandrel sufficient to provide clinically acceptable steerability,
(2) maintain the clearance between the catheter and guidewire components sufficient to provide clinically acceptable steerability and trackability,
(3) maintain the wall thickness of the inner member sufficient to provide clinically acceptable pushability, and
(4) maintain the wall thickness of the balloon component sufficient to provide clinically acceptable structural integrity and pressure tolerance. Thus, there exists a lower limit to the cross-sectional shaft and crossing profiles that can be achieved by further miniaturization of over-the-wire catheter systems of multi-channel design.

Prior Art Non-Over-the-Wire Systems

Given the limitations inherent to the process of miniaturization, and the continued demand for systems with progressively lower profiles, the fundamental design of the over-the-wire catheter system was reconfigured to enable the construction of dilatation balloon delivery systems with lower crossing and cross-sectional shaft profiles than heretofore possible. This effort resulted in the generation of the non-over-the-wire dilatation balloon catheter systems. As used herein, "non-over-the-wire" connotes a catheter system in which the catheter component cannot be separated from the guidewire component of the system.

Non-over-the-wire dilatation balloon catheter systems can be separated: (1) on the basis of the number of channels that extend throughout the respective systems, into single and multi-channel systems or, (2) on the basis of the mobility of the respective guidewire components into semi-movable, fixed-wire and balloon-on-a-wire systems. Semimovable catheter systems permit full rotational and limited coaxial mobility of the guidewire component with respect to the catheter component. Fixed-wire catheter systems permit varying rotational mobility, but do not permit coaxial mobility of the guidewire component with respect to the catheter component. Balloon-on-a-wire systems do not allow any significant mobility of the guidewire component with respect to the balloon component. Directional control of these devices requires rotation of the entire device —both catheter and balloon.

U.S. Pat. No. 4,616,653 describes a semi-movable multi-channel catheter system. Most balloon-on-a-wire catheter systems are single channel systems, for example as those shown in U.S. Pat. Nos. 4,838,268, 4,875,481, 4,896,670, 4,906,241, 4,917,088, 4,943,278, and 4,946,466. Single channel fixed-wire systems are shown in U.S. Pat. Nos. 4,573,470, 4,582,181, 4,664,113, 4,715,378, 4,723,936, 4,793,350, 4,846,174, 4,955,384 and Re 33,166, while multi-channel fixed-wire systems are described in U.S. Pat. Nos. 4,641,654, 4,892,519 and European application A1/0-374-859.

Improvements in the crossing profiles of non-over-the-wire systems have been achieved by reducing the diameter of the guidewire segment contained within the balloon, and also by reducing the thickness of the balloon material. Improvements achieved in this manner however are made at the expense of guidewire exchangeability. Thus, the use of a non-over-the-wire system obligates the operator to sacrifice intra-luminal access if an exchange procedure becomes necessary.

The progress that has been achieved in reducing the shaft profiles of non-over-the-wire systems relates to the development of single-channel systems. The prior art designs of multi-channel non-over-the-wire systems confer little benefit in proximal shaft profile, because the structure of these systems is subject to the aforementioned functional considerations. The gain in shaft profile achieved in the construction of selected prior art single-channel non-over-the-wire systems was accomplished at the expense of the directional control and structural integrity of these systems.

The construction of a single-channel guidewire-directed angioplasty catheter-guidewire system requires the creation of a liquid-tight seal at least within the distal aspect of the system. Typically, adhesives are used to create this seal in single-channel non-over-the-wire systems of the prior art. This approach effectively joins the balloon and guidewire components of these systems within the distal aspect of the system.

Bonding the balloon directly onto the guidewire compromises the efficiency with which guidewire-mediated rotational torque can be delivered to the distal aspects of these systems and thus compromises the steerability of these devices. When the balloon components of these devices "hang up" on the luminal surfaces of blood vessels, the adverse impact of this practice on steerability becomes particularly apparent. In this circumstance, the adhesive bond between the balloon and guidewire tethers the guidewire to the luminal surface of the blood vessel wall and further compromises the rotational torque that can be delivered to the distal aspects of these systems.

The practice of bonding the balloon directly onto the guidewire also subjects the balloon and guidewire components of these systems to shear forces during guidewire rotation. This predisposes these devices to balloon wrapping, balloon rupture and guidewire fracture. Torque limiters, for example as described in U.S. Pat. No. 4,664,113, can be used to prevent over-rotation of the guidewires, and preclude the development of structural damage to these systems due to excessive unidirectional guidewire rotation. Unfortunately, torque limiters complicate the angioplasty procedure by requiring the operator to stop the procedure periodically and unwind the guidewire to its "home" position as the operator navigates the catheter system through the convoluted arteries of the patient's cardiovascular system.

To summarize, generally non-over-the-wire systems can be constructed with lower cross-sectional shaft and crossing profiles relative to clinically acceptable over-the-wire systems. Reducing the profile of the segment of the guidewire that extends through the confines of the balloon component, reducing the balloon wall thickness, and reducing the number of channels from two to one all result in lower shaft profiles for these systems. The construction of a single-channel system requires the creation of a liquid-tight seal at the distal catheter-guidewire interface. Typically adhesives have been employed to create this interface within single-channel systems of the prior art. There exist several functional limitations that relate to the use of adhesives in creating this interface.

Venting Considerations for All Catheters

Air must be removed from the hydraulic channels of all dilatation balloon catheter systems before they are introduced into the vascular system. Failure to evacuate the air predisposes the patient to the risk of an air embolism in the event of a balloon rupture. In addition, air contained within the hydraulic channel compromises the hydraulic function and thus therapeutic effectiveness of these devices.

In general, the hydraulic channel of a conventional angioplasty dilatation balloon catheter is sealed at the distal end. Preparation of such a catheter for use in an angioplasty procedure is typically a two-step process. First, as much of the air contained within the hydraulic channel as possible is evacuated. This is generally accomplished by applying a syringe to the proximal end of the hydraulic channel and aspirating the contents. Next, the channel is filled with dilute contrast media, a relatively viscous solution. Introduction of contrast media in the setting of incomplete evacuation usually traps air in the balloon and creates an air bubble. Selectively air-permeable, liquid-tight vents were developed to enable air, trapped within the distal confines of hydraulic channels of dilatation catheters, to escape when these devices are prepared with contrast. These vents take advantage of the fact that the viscosity of a fluid exceeds that of a gas.

One example of a vented over-the-wire catheter is described in U.S. Pat. No. 4,638,805. In this patent, a small passageway is provided from the lumen of the balloon to the tip of the catheter. The passageway is formed by placing a very small diameter wire between the distal aspect of the balloon and the central column within the balloon that contains the guidewire. When the catheter is manufactured, the balloon and the central column are heat-shrunk together with the wire in place. The wire is later removed to create a small passageway for the exit of air from the balloon during filling of the balloon. By making the passageway sufficiently small, fluid is retained within the balloon while air can be expelled therefrom.

U.S. Pat. No. 4,811,737 describes an alternative method for venting an over-the-wire catheter. This patent describes a catheter with a small slit in the exterior surface of the balloon. When fluid is introduced into the balloon, air is forced out of the small slit. The inflation fluid is sufficiently viscous to prevent its escape through the same slit. Unfortunately, the slit creates a region in the surface of the balloon which is prone to failure. When the balloon is inflated to pressures of many atmospheres, the stresses are concentrated at the ends of the slit, making it prone to rupture.

U.S. Pat. No. 4,821,722 describes the use of micromachined openings in the central shaft and balloon surface for the purpose of selectively venting air from the hydraulic channel of an over-the-wire dilatation balloon catheter. The openings are sufficiently large to allow the flow of a gas therethrough, and yet sufficiently small to prevent the inflation fluid from escaping from the confines of the hydraulic channel.

U.S. Pat. No. 4,715,378 describes a vented fixed-wire device. In this patent, a winding passage extending through the bond between the guidewire coil and the distal aspect of the catheter functions as a vent. This device does not appear to have a torque limiter and hence it is prone to over-wrapping of the balloon with possible rupture of the balloon and/or fracture of the guidewire.

U.S. Pat. No. 4,793,350 describes another approach for venting a fixed-wire device. In this patent, a vent is formed by providing a small space between the guidewire and the distal aspect of the balloon. The catheter and guidewire are fastened together at the distal aspect of the balloon and this device contains a torque limiter.

Conclusion

From the foregoing, it is evident that there exists a continued demand for angioplasty dilatation balloon catheter systems that can be constructed with progressively lower cross-sectional shaft and/or crossing profiles. From the foregoing, it becomes evident that there exists a lower limit to the shaft profile that can be achieved in the construction of clinically acceptable guidewire-directed, hydraulically competent multi-lumen dilatational balloon catheter systems of the prior art (to include "over-the-wire," "mono-rail," "semi-movable" and selected "fixed-wire" catheter systems) given the limitations of current technology. From the foregoing, it becomes evident that clinically acceptable single-channel systems (to include "balloon-on-a-wire" and selected "fixed-wire" systems of the prior art) can be constructed with lower cross-sectional shaft profiles relative to clinically acceptable multi-channel systems. From the foregoing, it becomes evident that there exist several functional limitations inherent to the construction of prior art single channel catheter systems that relate to the practice of bonding the guidewire components to the balloon/catheter components in the construction of these systems. From the foregoing, it further becomes evident that it is desirable to vent the air from the hydraulic channels of balloon dilatation catheters.

From the foregoing, it becomes evident that there exists the need for novel designs that enable the construction of self-vented, guidewire-directed, hydraulically competent over-the-wire, mono-rail, and semi-movable dilatation balloon catheter systems with lower shaft profiles relative to the prior art, designs that do not require compromising the performance features of the various systems to achieve this end. From the foregoing, it becomes evident that there exists the need for novel designs that enable the construction of self-vented fixed-wire and balloon-on-a-wire catheter systems with superior directional control and structural integrity relative to the prior art that do not require compromising the shaft profiles of the respective systems to achieve this end. Below we describe a seal of our design, for use in the construction of catheters, that makes possible these and other improvements.

SUMMARY OF THE INVENTION

This invention resides in a seal for medical devices, primarily such devices as catheters, catheter systems and catheter accessories. One feature of the seal is the fact that it is formed between two parts of the device which are movable relative to each other, and potentially separated by a gap. Despite this movability and gap, the seal may be both gas-tight and liquid-tight under normal conditions of use of the medical device, or selectively permeable to gases while being liquid-tight. The invention has application to catheters, particularly medical interventional catheters, such as balloon dilatation catheters, including percutaneous transluminal coronary dilatation catheters, peripheral vascular transluminal dilatation catheters, valvuloplasty catheters, intracranial intravascular dilatation catheters, genitourinary dilatation catheters, laser ablation catheters, fiber-optic intravascular catheters, rotational ablation catheters, intra-aortic balloon dilatation catheters, and atherectomy catheters. In addition, the invention has application to composite catheter systems including guiding catheter/dilatation balloon systems, laser delivery/dilatation balloon systems, atherectomy/dilatation balloon systems, intravascular ultrasound/dilatation balloon systems, angioscopy/atherectomy systems, and angioplasty dilatation balloon/guidewire systems, including over-the-wire, semi-movable, fixed-wire and balloon-on-a-wire catheter/-guidewire systems.

According to the invention, the seal, whether it be a selectively gas-permeable, liquid-tight seal or a gas-tight and liquid-tight seal is created by the precise juxtaposition of two or more independently movable surfaces. The seal separates two regions of the device, one of which may be defined as a high pressure region since it will at times retain a fluid (generally a liquid) at a pressure higher than the other region, and the other may accordingly be defined as a low pressure region. Depending on the particular configuration of the surfaces and the movable parts supporting the surfaces, the effectiveness of this seal will depend upon one or more of the following: (1) the proximity of the two surfaces that comprise the interface, i e , the gap width; (2) the surface area common to the interface, i.e., the portions of the two surfaces which directly face each other and are separated only by the gap; (3) the pressure differential applied across the interface, i.e., the difference in pressure between the high and low pressure regions; (4) the viscosity of the liquid contained by the interface, i.e., retained in the gap between the surfaces; (5) the surface tension of the liquid; and (6) the wettability of the surfaces on either side of the gap. The gap will be sufficiently narrow such that when a sealing liquid, which may be either the same liquid retained in the high pressure region or a lubricating liquid distinct from that liquid, is retained therein, the sealing liquid will block the passage of any liquid through the gap so long as the difference in pressure between the high and low pressure regions is below a maximum pressure differential. This maximum pressure differential may be selected as a matter of choice. In most applications the maximum pressure differential will range from about 2 atmospheres to about 50 atmospheres, preferably from about 5 atmospheres to about 20 atmospheres. The maximum gap width which will achieve the desired sealing effect will vary as a function of the smoothness of the sealing surfaces. In any event, seals according to this invention are sufficiently liquid-tight for most interventional catheters.

A seal in accordance with this invention which is described as being both "gas-permeable" and "liquid-tight" is one in which the gap between the two surfaces initially contains no liquid at all, but instead merely air. As the catheter is being charged with liquid to prepare it for use, the gap becomes filled with the liquid. Prior to this occurring, however, all air or other gas present in the interior of the catheter escapes through the gap. Once all gases have escaped and the gap is filled with liquid, the retentive forces of the sealing surfaces inhibit the passage of further liquid into or out of the gap, despite a pressure differential from one end of the gap to the other. A seal in accordance with this invention which is described as being both "gas-tight" and "liquid-tight" is one in which the gap is initially filled with a lubricant, either solid or semi-solid, which blocks passage of both liquid and gas. The lubricant will be a substance other than the liquid which has been placed inside the catheter interior.

The viscosity of the liquid occupying the gap between the sealing surfaces is often significant to the effectiveness of the seal. When this liquid is the same liquid which is being retained by the seal in the high pressure region, the seal of this invention will generally be constructed to retain liquids having a viscosity of at least about the viscosity of water 20° C., i.e., 1 centipoise. The physical parameters and dimensions of the seal in preferred embodiments of the invention will be such that the seal will effectively retain liquids having a viscosity equal to or greater than approximately 2 centipoise, and most preferably equal to or greater than approximately 4 centipoise. In the typical contemplated usage of the seal in medical catheters, the liquid will have a viscosity of approximately 6 centipoise.

The optimal gap width for any particular application may vary depending on the other parameters of the seal. In most applications, best results are achieved with a gap of less than about 0.005 cm, preferably from about 0.0001 cm to about 0.005 cm, more preferably less than about 0.0025 cm, and most preferably from about 0.00025 cm to about 0.0025 cm.

Various additional preferred embodiments of the invention will be apparent from the succeeding section of this specification. Included among these are embodiments in which the gap is of uniform width along the facing areas of the sealing surfaces, and those in which the gap varies in width. The two surfaces will generally be complementary in contour, however. In certain embodiments, one or both of the surfaces will be adjacent to surfaces which are not complementary in contour to the opposing surface, and the parts will be movable in such a manner as to vary the areas of the complementary surfaces which directly face one another. By varying the relative positions of the surfaces in this manner, the seal can be made to intentionally permit the liquid to leak through at a controllable rate.

In preferred embodiments of this invention, the use of a seal of this nature in the construction of catheters and catheter systems permits the generation of selectively gas-permeable, liquid-tight channels within such devices that contain surfaces that are movably disposed relative to one another. The use of a seal of this nature in the construction of catheters or catheter systems eliminates the need to separate hydraulic channels from other channels containing components (e.g., guidewires, etc.) that are movably disposed therein or therethrough. As a result, this seal enables the construction of hydraulically competent dilatation balloon catheter/-guidewire systems that contain independently movable guidewires and have single-channel shafts. This seal makes possible the construction of hydraulically competent single-channel over-the-wire, mono-rail and semi-movable catheter/-guidewire angioplasty systems. This makes possible the construction of these systems with a superior combination of shaft profile, pushability, hydraulic performance, steerability and trackability than theretofore possible. Furthermore, this seal eliminates the need to bond the balloon to the guidewire in the construction of single-channel fixed-wire and balloon-on-a-wire catheter systems. This makes possible the construction of these systems with superior steerability and structural integrity relative to corresponding single-channel systems of the prior art. In addition, this seal makes possible the construction of dilatation balloon catheters that do not conform to any currently recognized functional category. Finally, this seal provides a means of venting air from the confines of the hydraulic channels of dilatation balloon catheters in general and thus expedites the preparation and contributes to the safety of these systems.

In further preferred embodiments of this invention, the seal is located at the distal end of the balloon, and regardless of whether the catheter is of a fixed-wire, semi-movable or over-the-wire construction, the two surfaces of the seal are capable of a relative axial movement. This occurs for example when one surface of the seal is a smooth surface of the catheter guidewire and the other is a short length of tubing affixed to the interior of the catheter at the distal end of the balloon. In such embodiments it is important that the balloon be maintained in an elongated configuration while the catheter is being inserted into the vasculature and positioned inside the stenosis. Collapse of the balloon in the axial direction back along the guidewire will impede the effectiveness of the procedure. Maintenance of this elongated configuration, or column support, is achieved in a variety of ways in accordance with this invention, as will be explained in the section which follows.

Throughout this specification and the appended claims, the terms "distal" and "proximal" are used to designate the relative ends of components, sections or parts of the catheters. These terms are used in the sense in which they are widely used and well recognized among those knowledgable in the field of medical catheters. The "distal" end of any of these components, sections or parts refers to the end furthest inside the vasculature when in use and furthest away from the physician or other medical technician operating the catheter, whereas the "proximal" end refers to the opposite end, i.e., the end closest to the physician or technician.

The use of a gas-permeable, liquid-tight seal consisting of a plurality of surfaces that are independent and movable relative to each other is a profound departure from convention. As indicated previously, adhesives and or other bonds are almost universally used to create conventional seals, a practice that clearly does not permit the independent movement of the component surfaces that converge in the region of these seals.

The use of our seal in the construction of catheters provides several advantages that will endure the advent of new manufacturing techniques and new synthetics, developed with the aim to reduce conventional catheter shaft profiles and enhance catheter performance because many of these advancements can be applied to the manufacture of the catheters described herein. Although our seal has application to any medical catheter that contains a hydraulic channel, below we focus on the application of this seal to the construction of angioplasty dilatation balloon catheters and catheter systems. The benefits afforded by the incorporation of this seal in these catheters and catheter systems is described in the following text and figures.

BRIEF DESCRIPTION OF THE DRAWINGS

FIGS. 1A–1D illustrate multiple views of a prior art over-the-wire angioplasty dilatation balloon catheter.

FIGS. 2A–2N illustrate conceptual views of our invention.

FIG. 20 illustrates embodiments of the invention in various configurations in catheters.

FIGS. 3A-3D illustrate an intravascular catheter system containing a gas-permeable, liquid-tight seal at each end of the catheter.

FIG. 3E illustrates a prior art coaxial multi-channel catheter cross section.

FIGS. 3F-3J illustrate cross-sectional profiles of various embodiments of our invention.

FIGS. 4A-4I illustrate distal portions of over-the-wire and mono-rail catheter/guidewire systems where the seal is used as a vent.

FIGS. 8A-8C illustrate detailed full length views of a semi-movable dilatation balloon catheter/guidewire system containing either a fully retracted or fully advanced guidewire.

FIGS. 12A-12E illustrate a series of guidewire configurations useful in conjunction with catheters shown in other figures.

FIGS. 13A-13K illustrate a series of balloon-on-a-wire systems.

FIGS. 14A-14B are schematic views of a conventional prior art complete balloon angioplasty catheter system.

FIGS. 14C-14G illustrate the applicability of seals of our invention to the construction of composite catheter systems.

DESCRIPTION OF SPECIFIC EMBODIMENTS OF THE INVENTION

Overview of the Seal

Figure 5:
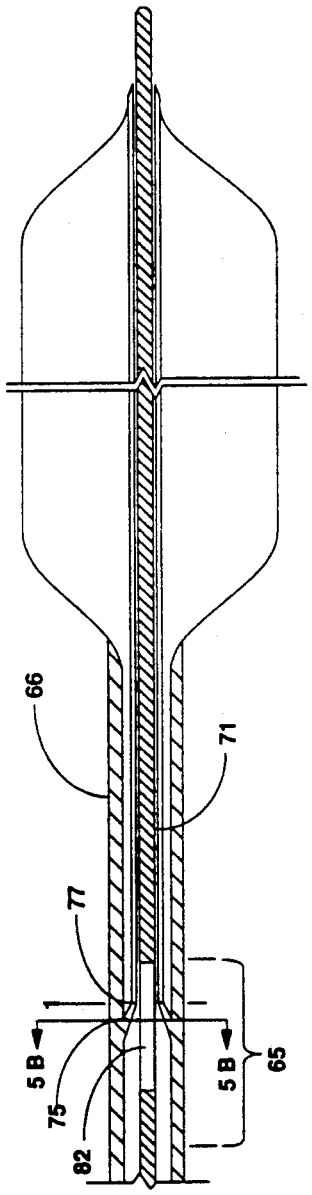
FIGS. 5A-5P illustrate distal portions of over-the-wire and mono-rail catheter/guidewire systems.
FIGS. 5Q-5R illustrate the mid-shaft and distal portions of a single-channel mono-rail catheter/guidewire.
Figure 5:
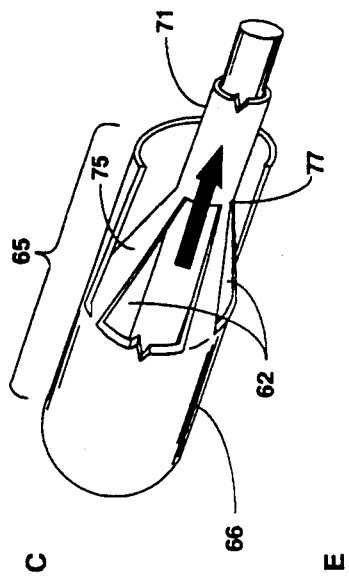
Figure 5:
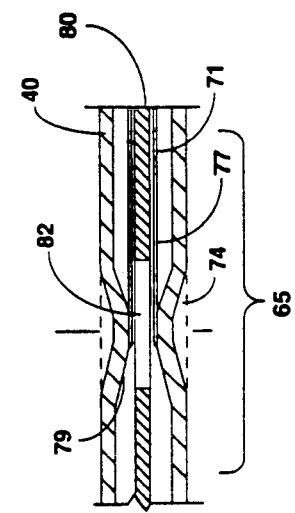
Figure 5:
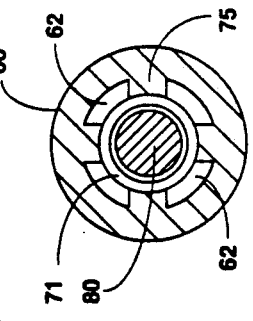
Figure 5:
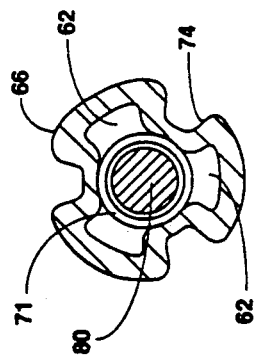
Figure 5:
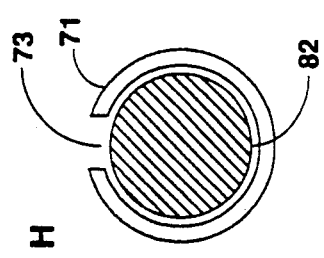
Figure 5:
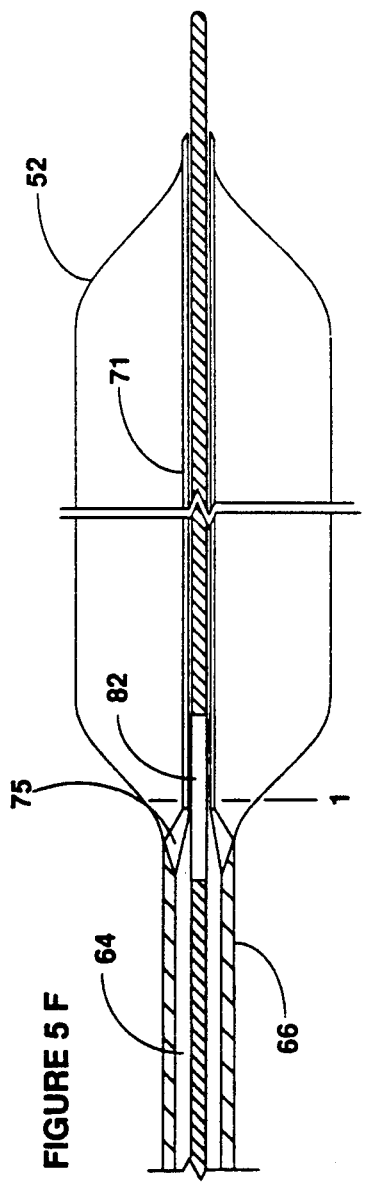
Figure 5:
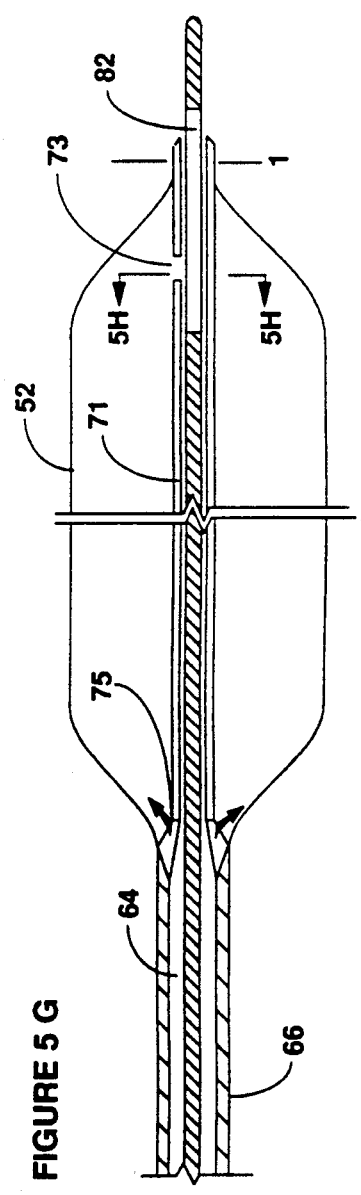
Figure 5:
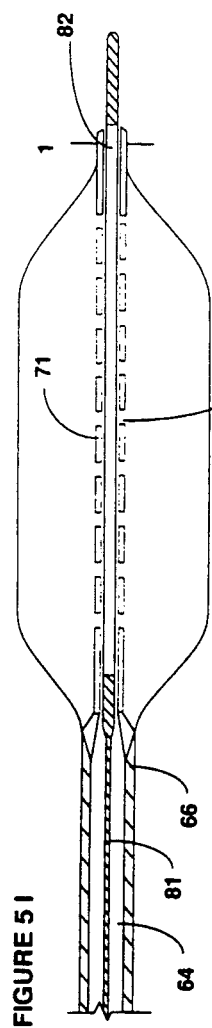
Figure 5:
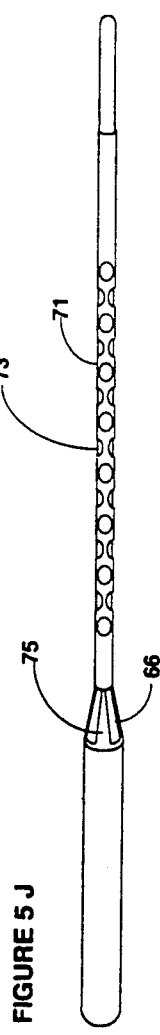
Figure 5:
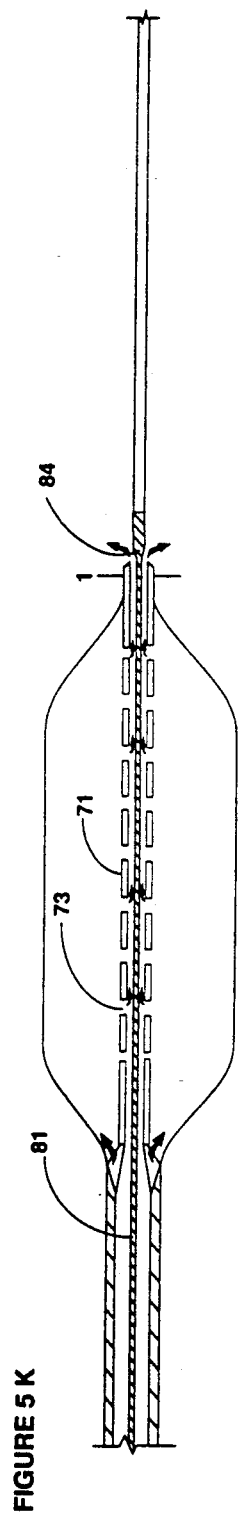
Figure 5:
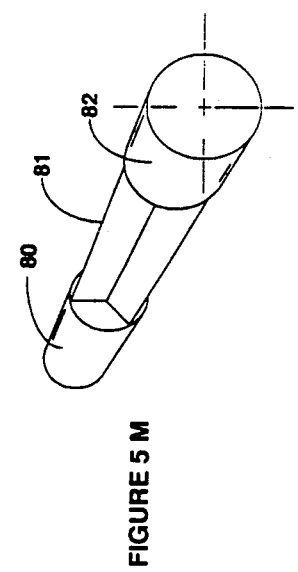
Figure 5:
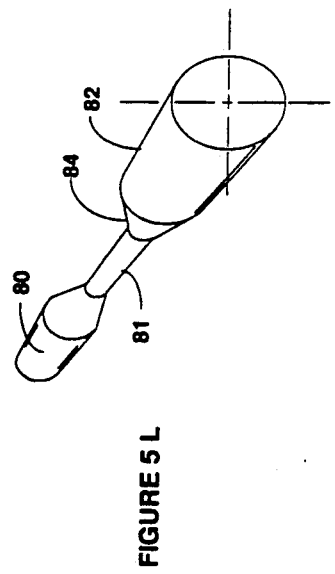

The following describes the preferred embodiments of several over-the-wire and non-over-the-wire dilatation balloon catheters that provide a superior combination of profile and performance features relative to conventional catheters of comparable functional class. Important features of each catheter include: (1) one or more selectively air-permeable, liquid-tight seals consisting of a plurality of independently movable surfaces and (2) a means of providing column support for the balloon, which means does not limit the rotational and/or coaxial mobility of the guidewire relative to the balloon.

As shown in FIG. 2, particularly FIGS. 2A-2N, a gas-permeable, liquid-tight seal can be created by the precise juxtaposition of two (or more) reciprocal surfaces. FIG. 2A illustrates a seal consisting of two surfaces 5 in proximity, to contain a liquid. The competence of this seal varies as a function of at least the following parameters: the degree of separation S between the two (or more) surfaces 5 that comprise the interface, the surface area common to the interface, the viscosity of the fluid contained by the interface, and the pressure differential applied across the interface. In general, the competence of the seal is directly related to the common surface area and liquid viscosity and inversely related to the degree of separation, and pressure differential. The degree of separation S between the sealing surfaces, in turn, is effectively related to the smoothness and wettability of the sealing surfaces.

Although depending upon manufacturing tolerances leakage may be inevitable with a seal of this design, a seal can be constructed in this manner that provides sufficient liquid retention to meet the functional requirements of interventional catheters. In general, interventional catheters are prepared with contrast media, a particularly viscous liquid that is relatively easily contained by a seal of this nature.

In the preferred embodiment, the components of this seal are movable relative to one another, and the seal itself is selectively liquid-tight, but typically not gas-tight. Both of these aspects can be satisfied by providing the proper separation between the two surfaces that comprise the interface. To be effective for most of the catheters described herein, the surfaces that comprise the seal must be positioned sufficiently close together to create a liquid-tight seal, and yet sufficiently far apart to permit the passage of air and free movement of the components. The selectivity of the seal takes advantage of the fact that the viscosity of a liquid consistently exceeds the corresponding property of a gas.

A functional seal can be created by the juxtaposition of any two surfaces, of almost any configuration, that have sufficient surface areas which are complementary in contour, i.e., that are separated by a narrow gap of substantially constant width (See FIGS. 2A-2N.) In the preferred embodiment, the interface consists of a rod 6 contained within a sleeve 7, as shown in FIG. 2B. This configuration provides an interface with elements that are both slidably and rotatably movable relative to one another.

Although alternative designs exist, they do not provide commensurate intercomponent mobility relative to the interface illustrated in FIG. 2B. Nonetheless, these designs could be used in the construction of catheter systems wherein it would be desirable to install a seal of our design and full coaxial and/or rotational guidewire mobility is not required. For example, a configuration of our seal that provides full rotational mobility and yet no coaxial mobility between the composite surfaces of the seal, could be used in the construction of fixed-wire and balloon-on-a-wire devices. Some of these designs are discussed below. The embodiment illustrated in FIGS. 2E-2F provides an interface consisting of two independent structures that are slidably and yet not rotatably movable relative to one another. The embodiment illustrated in FIGS. 2G-2H provides an interface consisting of two independent structures that are rotatably movable and yet not slidably movable relative to one another. The embodiment illustrated in FIGS. 2I-2J provides an interface consisting of two independent structures that are rotationally, and yet not slidably disposed relative to one another. The embodiments illustrated in FIGS. 2K-2N provides an interface consisting of two independent structures that are rotatably and yet not slidably disposed relative to each other. Additionally, the competence of these latter seals (e.g., FIGS. 2K-2N) requires the application of a force, commensurate with the opposing force created by the pressurized liquid contained therein, to maintain the competence of the respective seals 1.

The seal described herein provides a gas-permeable, liquid-tight seal between two structures that are movable with respect to one another within individual catheters or catheter systems. For example, as shown in FIG. 20, the seal provides a liquid-tight seal between the catheter and its associated guidewire. In this catheter, the central component of the seal consists of a smooth segment 82 of the guidewire 80, while the peripheral component 7 consists of a segment of tubing bonded to the luminal surface of the catheter. Preferably, the seal employs materials that are relatively non-compliant and have (or accept) a smooth surface. In the preferred embodiment, the surfaces common to the interface are smooth. Of course, by extending the length of the sealing surfaces, increasing roughness can be tolerated. Malleable materials or inflatable components can be used to create seals that are liquid-tight. These components, however, may require compression to maintain the seal. As a result, more friction will occur between the surfaces common to the seal.

In the preferred embodiment, polyimide and stainless steel are used for the seal components. Both polyimide and stainless steel can be manufactured to high tolerances and thus are well suited for the construction of the interface described herein. Each material can be formed into rods or thin-walled tubular segments with highly uniform smooth sealing surfaces. Because polyimide is more resilient and less prone to kinking than stainless steel, preferred embodiments of the seal employ a stainless steel rod surrounded by a polyimide sleeve. Of course, other implementations and materials also can be used. In fact, any biologically compatible material that can be manufactured with sufficient tolerances to meet the requirements described herein can be used in the construction of the components of this interface. Although we refer to stainless steel and polyimide, it should be understood that the construction of the seal is not limited to these two materials alone.

Satisfactory stainless steel and polyimide components can be purchased from precision vendors. In addition, a variety of methods can be used to construct reciprocal components of an interface, including heat shrinking, potting, precision injection molding, and high tolerance extrusion. Finally, in some embodiments a biologically compatible and suitable viscous lubricant is applied to the common surfaces of the interface to provide a seal that is both fluid-tight and gas-tight.

In further preferred embodiments of the invention, the seal consists of a sleeve, preferably polyimide, of at least about 0.3 cm, most preferably about 0.5 cm to 2 cm, in length, surrounding a smooth rod, preferably stainless steel, of about 0.003 inch to about 0.040 inch (0.0076 cm to 1.02 cm), most preferably about 0.005 inch to about 0.010 inch (0.013 cm to 0.025 cm) in diameter, the annular space between the sleeve and the rod having a width of from about 0.0001 inch to about 0.001 inch (0.00025 cm to 0.0025 cm), most preferably from about 0.001 inch to about 0.0001 inch (0.0025 cm to 0.00025 cm). Such a seal permits air to escape and permits the rod and sleeve to move independently, and yet it retains a liquid mixture of 25% contrast media/75% saline. With such a mixture on one side of the seal and a pressure drop of 10 atmospheres across the seal, no significant drop in pressure or loss of liquid occurs for more than two minutes. Angioplasty procedures are usually completed with lower pressures and shorter balloon inflation times. Thus, the seal created by our interface is highly advantageous for use in angioplasty dilatation balloon catheters.

Although the manufacture of the interface requires some care, contrast media, the liquid commonly used to transmit hydraulic pressure within interventional catheters, is relatively viscous and therefore easily contained by a seal of our type. Thus, minor imprecisions generally do not affect the competence of the seal, enabling the ready use of mass production techniques for fabrication of the seals.

In an angioplasty catheter, a satisfactory seal between the guidewire and catheter requires a smooth surface on the guidewire in the region of the seal, which surface conforms to the luminal surface of the polyimide sleeve. Generally, the distal surfaces of guidewires of the prior art are not smooth, but are instead wrapped by metallic coils; these surfaces must therefore be modified accordingly. A variety of methods can be used to create guidewires that contain distal segments with uniform surfaces. In the figures, a clear zone indicates a smooth segment of the guidewire.

As shown in FIG. 20, the seal 1 can be placed at different locations along the length of a catheter. In the upper portion of FIG. 20, a seal 1 is shown at both the distal and proximal ends of the catheter and includes a smooth portion 82 (shown as a clear region in the drawings) of the guidewire. Portions of the guidewire referred to above as not smooth, such as the distal end 80, are indicated by shading with diagonal lines. In the middle portion of FIG. 20, a seal 1 is shown partway along the shaft of the catheter. Finally, in the lower portion of FIG. 20, a seal 1 is illustrated at both the distal end between the balloon and the guidewire and within the catheter shaft between the outer wall of the shaft and the guidewire. The latter seal enables the guidewire to exit the catheter wall.

In each portion of FIG. 20, the seal is established between a smooth region of the guidewire 80 and another portion of the catheter. The length of the smooth portion of the guidewire shown in FIG. 20 (and in all the other figures) is merely for illustration. As will be appreciated, the smooth portion of the guidewire may be extended as necessary to provide a seal over a longer range of movement. For example, in the upper portion of FIG. 20, the seal 1 at the distal aspect of the balloon portion 50 of the catheter is shown as approximately 1 cm in length. In some embodiments of the invention, the seal may extend over a considerably longer portion of the length of guidewire 80, depending primarily upon the extent to which it is desired to advance the guidewire 80 beyond the distal tip of the balloon. For example, if it is desired to advance guidewire 80 beyond the tip of the balloon by 20 cm, then about 20 cm of the guidewire will be rendered smooth.

Overview of the Application of Our Seal to the Construction of Catheters

Our seal eliminates the need to separate hydraulic channels from other channels containing components (e.g., guidewires, etc.) that are movably disposed therein or therethrough and yet does not sacrifice mobility of those components. This seal eliminates the need to separate the guidewire channel from the hydraulic channel of over-the-wire, mono-rail and semi-movable catheter-guidewire angioplasty systems and thereby makes possible the construction of these systems with single channels. This in turn allows the construction of these catheter systems with a superior combination of shaft profile, pushability, hydraulic performance, steerability and trackability than previously possible.

Our seal further eliminates the need to bond the balloon to the guidewire in the construction of single-channel fixed-wire and balloon-on-a-wire catheters. This in turn allows the construction of these systems with superior steerability and structural integrity than previous single-channel systems of comparable functional class. Additionally our seal enables the construction of dilatation balloon catheters that have unique, previously unobtainable, configurations. Finally, our seal provides a means of venting air from the hydraulic channels of dilatation balloon catheters. This expedites their preparation and contributes to the safety of these devices. Furthermore, our seal is relatively simple to manufacture with techniques amenable to mass production using commercially available components.

FIGS. 3A–3D illustrate a single-channel hydraulically competent angioplasty catheter-guidewire system of our design, which system contains two gas-permeable, liquid-tight seals 1 disposed at each end of the catheter and an independently movable guidewire. These figures have been included to illustrate the impact of our seal on the structure and function of guidewire-directed angioplasty dilatation balloon catheter systems. FIG. 3A is a side view of the entire system. FIG. 3B is a detailed side view of the distal aspect of the system. FIG. 3C is an end view and FIG. 3D is a cross-sectional view of the catheter shaft. Also shown is a means 71 for providing column support to the balloon 52, while permitting independent mobility of guidewire 80, which means is secured to the shaft 66 of the device by joint 72. A fenestration 73 within the distal aspect of support means 71 enables evacuation of air from the balloon 52. In this example, portions 82 of guidewire 80 are smooth and function as the central components of the seals 1. The guidewire 80 slides within two polyimide sleeves 7 bonded to the singular luminal surface of the catheter at opposite ends of the device.

The catheter depicted in FIGS. 3A–3D represents a significant departure from prior art angioplasty dilatation balloon delivery systems such as over-the-wire, mono-rail and semi-movable catheters, that provide variable coaxial and independent rotational guidewire movement, because the shaft 66 contains a singular multi-purpose channel 64 that conveys hydraulic pressure and accommodates a movable guidewire 80. As discussed, typical prior art systems that provide independent coaxial or rotational guidewire mobility contain multiple channels. The gas-permeable, liquid-tight interface 1 of our invention enables the fabrication of hydraulically competent single-channel dilatation balloon delivery systems that provide independent (to include both coaxial and rotational) guidewire mobility because this approach circumvents the need to separate the guidewire channels from the hydraulic channels in the construction of these systems.

FIGS. 3E–3J have been included to provide some perspective concerning the functional advantages inherent to the construction of over-the-wire, semi-movable and mono-rail dilatation balloon delivery systems with single versus multiple channel shafts. FIG. 3E is a cross-sectional view of a prior art low profile multi-channel over-the-wire, semi-movable or mono-rail catheter shaft. With respect to mono-rail systems, illustrations 3E–3H and 3J illustrate the relevant portion of the catheter shaft that encompasses the guidewire, i.e., the distal portion. FIG. 3I is a cross-sectional view of the proximal portion of a mono-rail catheter. FIG. 3F illustrates a cross-sectional view of the proximal portion of a single-channel shaft of an over-the-wire, semi-movable or mono-rail catheter of our design of comparable external profile to the device illustrated in FIG. 3E. Note that the cross-sectional area of hydraulic channel 64 contained within our device is substantially larger than the corresponding area 46 contained within the prior art multi-channel device. Given the relationship between hydraulic performance and hydraulic channel cross-sectional area, our system allows construction of over-the-wire, semi-movable and mono-rail catheters with substantially faster balloon inflation/deflation rates and shorter balloon inflation/deflation cycle times than multi-channel devices of the prior art of comparable guidewire profile, shaft profile and external shaft wall thickness. Therefore, our seal enables the construction of over-the-wire, semi-movable and mono-rail catheters that provoke less interruption to blood flow at the beginning and end of the dilatation phase of coronary angioplasty than prior art multi-channel catheters of similar shaft profile. FIG. 3G illustrates a low shaft profile version of a catheter of our design with a hydraulic channel cross-sectional area that is commensurate with prior art. This figure illustrates that the use of our seal permits the construction of over-the-wire, semi-movable and mono-rail catheters with comparable hydraulic performance and significantly lower shaft profiles than previously available. FIG. 3H illustrates a catheter shaft of our invention with a lower overall profile and larger hydraulic channel cross-sectional area than previously possible. This figure illustrates that our seal allows construction of over-the-wire, semi-movable and mono-rail catheters with a superior combination of shaft profile and hydraulic performance characteristics than previously available.

FIG. 3J illustrates that our seal allows construction of single-channel over-the-wire, semi-movable and mono-rail catheter systems with a superior combination of shaft profile, hydraulic performance, pushability, steerability and trackability, than the prior art. The external shaft profile 69 in FIG. 3J is lower than the corresponding profile 49 in FIG. 3E, yet the wall thickness of tubular element 66 in FIG. 3J is greater than the corresponding wall thickness of tubular element 44 in FIG. 3E. In addition, the cross-sectional area of hydraulic channel 64 in FIG. 3J exceeds the corresponding area of channel 46 in FIG. 3E. The clearance between the catheter and guidewire in FIG. 3J exceeds the corresponding clearance in FIG. 3E. Finally, the profile of guidewire 80 in FIG. 3J exceeds the corresponding profile in FIG. 3E. Given the relationships between wall thickness and pushability, between hydraulic channel cross-sectional area and balloon hydraulic performance, between catheter-guidewire clearance and both steerability and trackability, and the relationship between guidewire profile and steerability, the use of our seal allows construction of single-channel over-the-wire, semi-movable and mono-rail catheters with a superior combination of shaft profile, pushability, hydraulic performance, steerability, and trackability than multi-channel catheters of the prior art.

The catheter depicted in FIGS. 3A-3D represents a significant departure from prior art angioplasty dilatation balloon delivery systems that contain single-channel shafts, i.e., balloon-on-a-wire and selected fixed-wire systems. Unlike these prior art systems, the guidewire of our catheter can rotate independently within the shaft system. Typically, prior art systems that contain single-channel shafts do not provide independent guidewire rotational mobility. Our seal makes possible the construction of hydraulically competent single-channel angioplasty systems that afford independent guidewire mobility. This feature allows for the manufacture of balloon-on-a-wire and selected fixed-wire devices with markedly enhanced guidewire mobility and hence "steerability," relative to the prior art. This feature further allows for the manufacture of these devices with superior structural integrity relative to single-channel devices of the prior art. Finally, this feature eliminates the need for torque limiters in the manufacture of these systems. In summary, the use of our seal makes possible the construction of single-channel fixed-wire and balloon-on-a-wire systems with superior steerability and structural integrity relative to single-channel systems of the prior art.

Our seal further expedites the process of preparing balloon dilatation systems of our design with contrast medium. Because our seal is liquid-tight and not air-tight, air escapes from the hydraulic channels of dilatation balloon systems of our design, circumventing the need to apply a vacuum to the hydraulic channels of these devices prior to introduction of contrast medium. Therefore, the use of our seal provides catheters that are easier to prepare for insertion into the body and that are less likely to provoke air emboli in the event of a balloon rupture than corresponding prior art unvented devices.

In summary, our seal makes possible the construction of self-vented, single-channel, hydraulically competent, dilatation balloon catheter systems that contain independently movable guidewires disposed therethrough. The use of our seal permits the manufacture of self-vented, single-channel, hydraulically competent over-the-wire, semi-movable and mono-rail systems that provide a superior combination of shaft profile, pushability, hydraulic performance, steerability, and trackability relative to the prior art. The use of our seal permits the manufacture of self-vented, single-channel, hydraulically competent fixed-wire and balloon-on-a-wire devices that provide superior steerability and structural integrity relative to the prior art. The use of our seal further eliminates the need for torque-limiters in the manufacture of fixed-wire devices of our design. The use of our seal further makes possible the manufacture of a variety of catheter-guidewire systems that do not conform to any currently recognized functional category and that afford functional advantages relative to the prior art. Below we discuss a series of designs for over-the-wire, semi-movable, mono-rail, fixed-wire and balloon-on-a-wire dilatation balloon catheter-guidewire systems that contain our seal, as well as a series of systems that contain our seal that do not conform to any currently recognized functional category.

SPECIFIC EXAMPLES

The following examples describe the application of our seal to various catheters. The examples discussed include one or more air-permeable, liquid-tight seals of our design at the catheter-guidewire interface together with some means of column support for the balloon which means does not limit the rotational and/or coaxial mobility of the guidewire disposed therethrough. Several of the preferred embodiments include fenestrations within the balloon column support means for the selective evacuation of air from the balloon.

FIGS. 4A-4I illustrate the use of our seal 1 solely as an air vent for the hydraulic channels of over-the-wire or mono-rail dilatation balloon catheters that have relatively conventional multi-lumen catheter shafts. Because the seal is selectively liquid-tight, and not gas-tight, it is well suited for this purpose. Unlike the vents described in U.S. Pat. No. 4,821,722, the vents described in FIG. 4 do not rely upon the size of the hole in the central shaft for selective liquid retention. In the case of the catheters of our design, the interface between the guidewire and the central shaft functions selectively to permit the passage of air and retain liquid. The vents described in U.S. Pat. No. 4,821,722 rely upon the size of the holes formed in the central tubing for selectively passing air and not liquid. Hence, the approach described in U.S. Pat. No. 4,821,722 mandates the creation of extremely small holes in the central tubing. Our design functions with the use of holes in the central tubing that are large enough to permit the passage of liquid. This circumstance renders our vents easier to manufacture relative to the vents described in U.S. Pat. No. 4,821,722. In addition, our vents provide independent mobility of the vent components, whereas the vents described in U.S. Pat. No. 4,821,722 do not provide such mobility. In short, the vents described herein are functionally distinct, easier to manufacture, and provide superior inter-component mobility relative to the prior art means of venting the central shaft.

FIGS. 4A-4C illustrate a device that contains a fenestration 73 within the central tube of the catheter shaft 44 to permit the evacuation of air through a liquid-tight interface 1. When the balloon is filled with fluid before use, air escapes through the tip of the catheter. The vent consists of: (1) a smooth segment 82 of the guidewire 80 that is movably contained within a polyimide sleeve 71, (2) the polyimide sleeve 71 that is bonded to the luminal surface of the central tubular component 44 of the catheter shaft and (3) one or more fenestrations 73. A laser can be used to create the fenestration 73 within the central tubular element.

FIGS. 4D-4H depict various embodiments of this basic catheter design. FIG. 4D illustrates the use of a sleeve of polyimide tubing 71 with multiple fenestrations 73 in the construction of a segment of the central tubular component of the device. FIG. 4E is a perspective view of the same device. FIG. 4F illustrates the use of a fenestrated segment of polyimide tubing 71 that extends the length of the balloon. The polyimide tubing 71 replaces the distal portion of the central shaft 44. This provides a self-vented catheter with a crossing profile which is lower than those of conventional over-the-wire catheters.

FIG. 4H illustrates the use of polyimide tubing 71 for the construction of the entire central tubular element 44. This approach enables a vented over-the-wire catheter with a lower tip 51 profile and shaft profile 49, than previous devices.

FIG. 4I illustrates a catheter similar to the device depicted in FIG. 4H, except the fenestration 73 is within the midshaft of the device 40.

FIG. 5 illustrates a variety of over the wire or mono-rail systems in which the central polyimide tubular component 71 terminates within the shaft 40 of the device. The devices shown in FIG. 5 contain single multi-purpose channels 64 that accommodate guidewires and conduct hydraulic fluid and pressure. For the devices depicted in FIG. 5, the proximal end 77 of the central tubular element 71 is supported by a conical support structure 65 within the catheter shaft.

FIG. 5A illustrates the design of a catheter with a polyimide central tubular component 71 that extends into the mid-shaft of the catheter. This design permits the construction of a partially vented catheter that provides superior hydraulic performance than the device depicted in FIG. 4I of comparable external shaft profile and guidewire capacity. Compared to the devices in FIGS. 5F-5R, this device has a larger shaft profile and is easier to construct.

FIGS. 5B-5C and FIGS. 5D-5E illustrate alternative embodiments of the conical support structure 65. The structure 65 illustrated in FIGS. 5B-5C consists of a plurality of radial elements 75 that extend from the luminal surface of the catheter shaft tubing 66 to the outer surface of the polyimide support tubing 71. These elements, in combination, define a conical support structure 65 that contains spaces 62 which permit the passage of liquid and the transmission of hydraulic pressure. These spaces 62, however, are too small to permit the passage of guidewires introduced into this composite conical structure. In effect, the supporting elements 75 transmit column support from the catheter shaft 66 to the proximal end 77 of tubular support structure 71 while directing guidewires introduced therethrough into the lumen of the polyimide tubing 71, all without significantly compromising the hydraulic function of the catheter. FIGS. 5D and 5E illustrate an alternative embodiment for the conical support structure 65. Coaxial crimps 74 in the shaft tubing 66, disposed radially, as illustrated in FIG. 5D, support the proximal end 77 of tubular element 71. The spaces 62, defined by the luminal surface of tubular element 66 and the external surface of tubular element 71, permit the passage of hydraulic fluid and the transmission of hydraulic pressure. The proximal edges 79 of the crimps 74 function to direct guidewires advanced therethrough into the confines of tubular element 71.

FIGS. 5F-5R illustrate several over-the-wire or mono-rail catheter designs that contain polyimide central tubular components 71 terminating within the confines of the balloon 52. Compared to the device illustrated in FIG. 5A, the devices illustrated in FIGS. 5F-5R provide over-the-wire or mono-rail dilatation balloon catheter systems with lower cross-sectional shaft profiles, because they eliminate the overlap between tubular components 66, 71 in the shafts of these devices.

FIG. 5F illustrates a partially vented device constructed with an imperforate polyimide tube 71. FIGS. 5G-5H illustrate an alternative fully vented approach in which a fenestration 73 is provided at the distal end of the central tubular component 71 to allow evacuation of air from the hydraulic channel 64 and balloon 52.

FIGS. 5I-5M illustrate a fully vented over-the-wire dilatation balloon catheter-guidewire system that can be used to provide distal dye injection or that can be used as a "bail out" device. The majority of over-the-wire angioplasty catheter systems of the prior art provide distal dye injection. Such devices enable the operator to selectively inject contrast into the confines of the vessel lumen distal to the device and thereby further define the anatomy of the vessel lumen distal to the device. U.S. Pat. No. 4,790,315 describes a "bail-out" catheter. "Bail-out" devices are used to preserve perfusion to regions of the body subserved by vessels that are prone to collapsing in the aftermath of an angioplasty.

Typically, devices that permit balloon dilatation and distal fluid injection contain multi-lumen catheter shafts and hence their construction is subject to the foregoing limitations. In brief, these devices tend to have relatively large shaft profiles. Our device enables the construction of an angioplasty dilatation balloon catheter system that provides distal delivery of contrast, blood and blood substitutes with a superior combination of shaft profile and distal perfusion capacity relative to the prior art.

The catheter depicted in FIGS. 5I-5M is prepared with a guidewire that contains a segment 81 that does not conform to the luminal surface of the polyimide tubular component 71. Perspective views of two different configurations for segment 81 of the wire are shown in FIGS. 5L and 5M, where the views have been telescopically reduced in the axial direction to render all segments visible. Note that the non-conforming segments 81 are recessed such that when they are placed directly opposite the luminal surface 71 of the tubular component, considerable clearance for fluid flow remains. These non-conforming segments thus do not serve as part of the seal. By varying the coaxial relationship of the catheter and guidewire relative to each other, and thus the relative position of the non-conforming surface on the guidewire, one can close and open the seal and thereby select the function of the system. FIG. 5I illustrates the closed configuration in which these two components are aligned to provide a gas-permeable, liquid-tight seal 1 within the distal aspect of the catheter and to permit inflation of the balloon. The open configuration is achieved by advancing the wire through the catheter as illustrated in FIG. 5K, thereby allowing escape of the fluid contents of the hydraulic channel (e.g., contrast media, medications, blood products or blood substitutes) into the intravascular space distal to the device. Removal of the guidewire also permits the injection of fluid through the device with an enhanced flow rate. Thus, the single channel within this device accommodates a movable guidewire, transmits hydraulic pressure, and conveys contrast and other fluids into the intra-vasculature space distal to the device. This relative movement can also be done to an intermediate and variable degree resulting in limited escape of fluid at a rate depending on the proportions of conforming and non-conforming surfaces which are directly opposing each other, thereby providing a means of controlling the rate at which the fluid escapes into the intra-vasculature space. A similar effect can be achieved with a coiled section of the guidewire located adjacent to the smooth section, as shown in the other Figures. Moving the coiled section into the region inside the smooth section of the luminal surface 71 reduces the effectiveness of the seal, and by varying the degree of penetration of the coiled section into this portion of the lumen, one can control the rate at which liquid will pass through the seal.

Of note, this device can be adapted for use with an infusion pump. Specifically, an infusion pump can be used to force fluid (i.e., blood, blood substitutes, medications and/or contrast medium) through the confines of the multi-purpose hydraulic channel 64 that communicates variously with the balloon and the lumen of the vessel distal to the device. By adjusting the coaxial relationship of the guidewire relative to the catheter, and by adjusting the pressure generated by the infusion pump, a variety of combinations of distal flow rates and balloon inflation pressures can be achieved.

FIGS. 5N-5P illustrate a catheter system that is similar in function to the device depicted in FIGS. 5I-5M. In FIGS. 5N-5P, the guidewire 90 contains a lumen 92 to conduct fluid via multiple fenestrations 94 variously into the balloon, or distal vasculature, depending upon the coaxial relationship of the guidewire 90 and catheter. FIG. 5O is an off-center profile view of the device depicted in FIGS. 5N and 5P.

FIGS. 5Q-5R illustrate the use of two liquid-tight seals 1 disposed within the mid-shaft and distal aspect of a single-channel, low-profile, self-vented mono-rail catheter. This combination of seals 1 permits air and the guidewire to exit channel 64 within the shaft 66 without disrupting the hydraulic integrity of the system. Monorail systems permit manipulation of the catheter independently of the guidewire. Although conventional mono-rail devices exist, these devices have separate guidewire channels and hydraulic channels. In prior art mono-rail systems, the guidewire channels simply terminate within the midshaft. U.S. Pat. No. 4,762,129 describes a prior art mono-rail system. The use of our seal allows construction of self-vented mono-rail catheters with fewer channels than previously possible. This provides these devices with a superior combination of shaft profile, hydraulic performance, steerability, and trackability compared to mono-rail devices of the prior art. FIG. 5Q depicts a mono-rail system with one type of distal catheter configuration incorporating a seal in accordance with this invention. Alternatively, each of the distal catheter configurations depicted in FIGS. 4A-5P can also be adapted for incorporation into mono-rail catheter systems by methods apparent from the structures themselves.

FIGS. 6A-6G illustrate a series of different catheters that can be withdrawn over a guidewire. These devices do not conform to any currently recognized functional class of catheter and do not accept the reintroduction of a guidewire therethrough. If a catheter exchange is anticipated, catheters of these types must be used with exchange wires or extendable guidewires. The performance of a catheter exchange with one of these devices, prepared with a standard non-exchange or non-extendable guidewire, requires sacrificing intra-luminal access.

Figure 6:
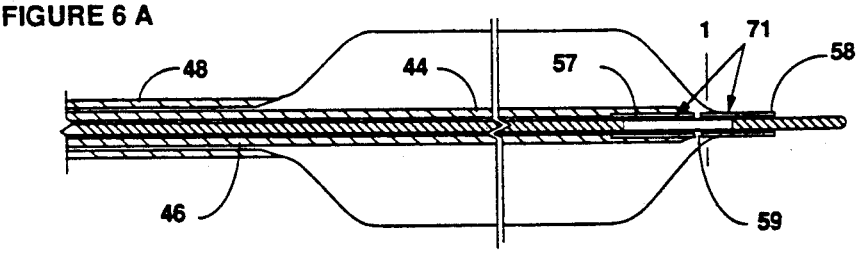
FIGS. 6A-6G illustrate distal portions of catheters which can be withdrawn over a guidewire, but do not permit the reintroduction of a guidewire.
Figure 6:
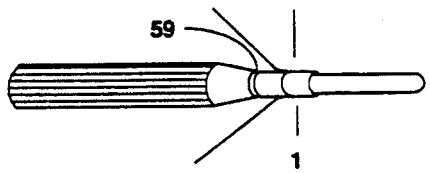
Figure 6:
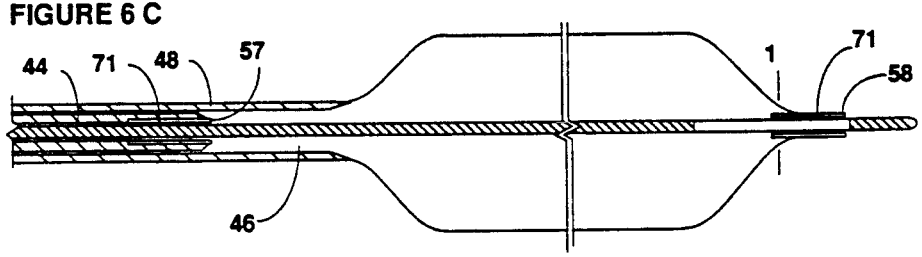
Figure 6:
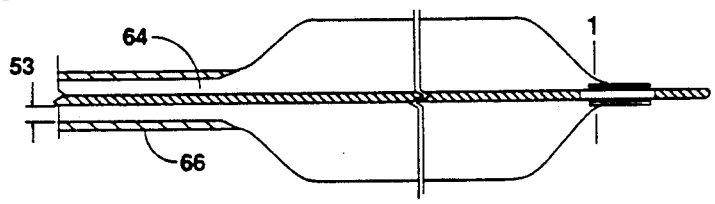
Figure 6:
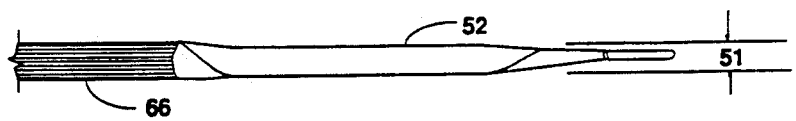
Figure 6:
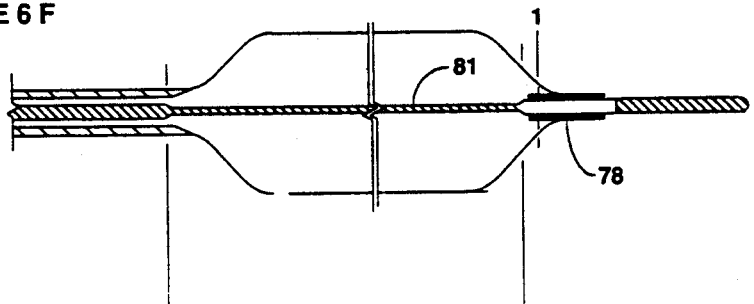
Figure 6:
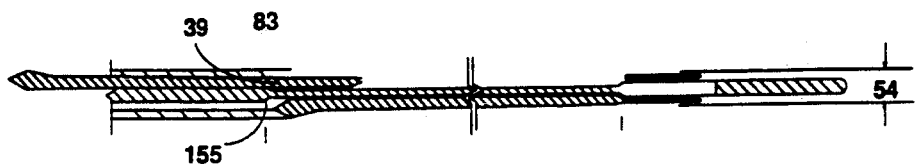
Figure 7:
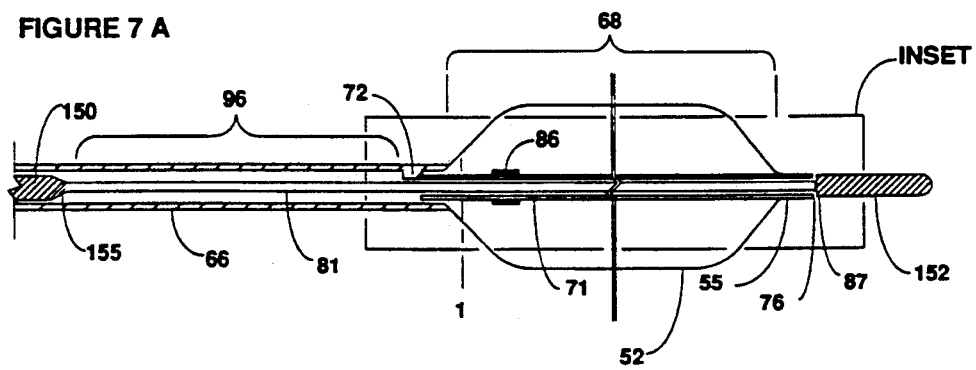
FIGS. 7A-7F illustrate distal portions of a series of semi-movable and fixed-wire dilatation balloon catheter/guidewire systems.
Figure 7:
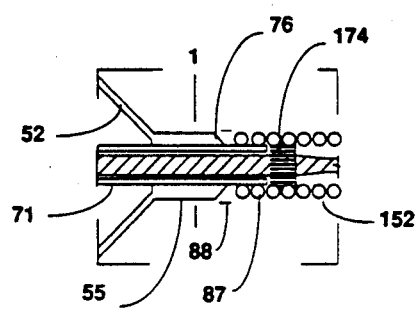
Figure 7:
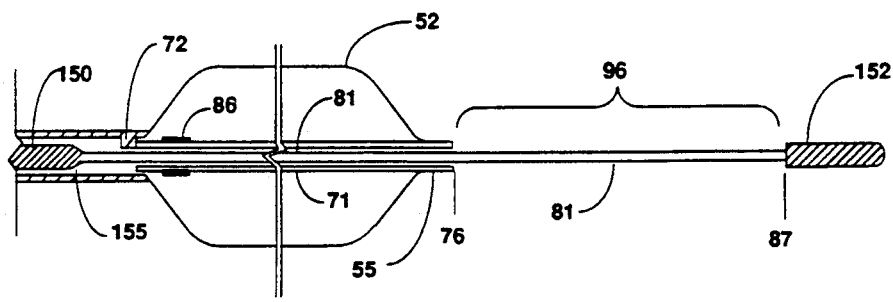
Figure 7:
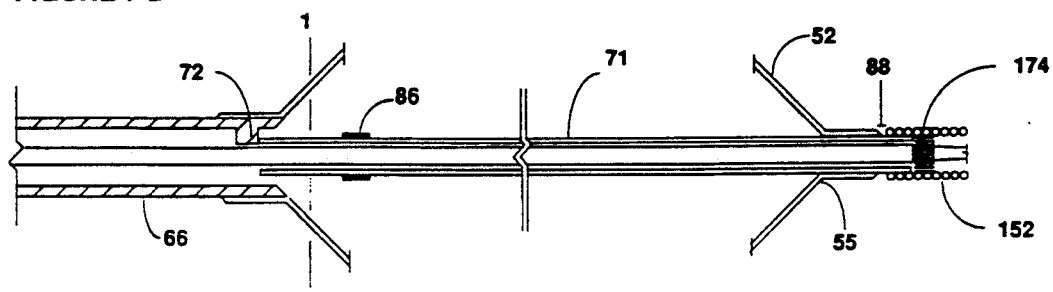
Figure 7:
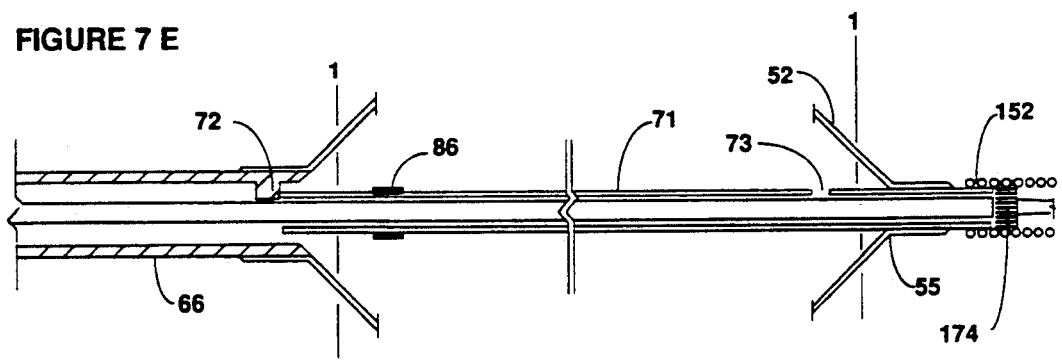
Figure 7:
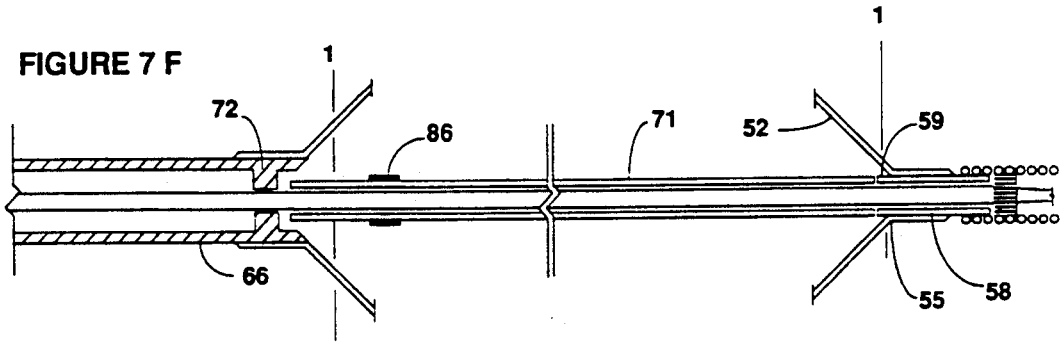

FIG. 6A illustrates a device that is similar to the device depicted in FIGS. 4A-4C. In FIG. 6A, however, the polyimide sleeve 71 that comprises the peripheral component of seal 1 is separated into two sleeves 57, 58 of similar dimensions. One sleeve 58 is bonded to the luminal surface of the balloon and the other sleeve 57 is bonded to central tubular component 44 of the catheter shaft. This configuration permits partial withdrawal of the central tubular component 44 of the shaft without disrupting the hydraulic integrity of the composite system. (See FIGS. 11E-11F for profile views of the proximal aspect of this device.) FIG. 6B is a perspective view of the catheter showing the split 59 between the portion 58 of polyimide sleeve attached to the distal lumen of the balloon and the portion 57 attached to the lumen of component 44. The design of the device depicted enables the operator to withdraw the central tubular component 44, as shown in FIGS. 6C and 6D, once it is no longer required. As indicated previously, the central tubular component 44 provides column support for the balloon component during the process of introducing the catheter across the confines of an intravascular lesion. Following proper placement of the catheter within the lesion, however, column support is not required, and component 44 not only confers little benefit, but limits the hydraulic performance of the device. The configuration shown permits the operator to advance the device intact, and then remove the central component 44, thereby enhancing hydraulic performance, without compromising hydraulic integrity. This embodiment provides a self-vented, high performance, low shaft profile angioplasty device that can be fully withdrawn over a guidewire, yet permits an exchange procedure when prepared with an extendable or exchange guidewire.

FIGS. 6D-6E are side views of a self-vented, low-profile, single channel device. No structures within balloon 52 provide column support for the balloon. The column support of the balloon 52 comes from the wrapped configuration of the balloon itself, a configuration that can be maintained by using reversible bonding agents or other temporary means. Wrappable balloons of this description are known in the art, and the known techniques of shaping, preparing and bonding such balloons are applicable in the practice of the present invention as well. The use of our seal in conjunction with reversible bonding of the balloon enables the construction of an angioplasty dilatation balloon catheter that is lower in both shaft and crossing profile than prior art systems that permit complete separation of the catheter component from the corresponding guidewire component. In addition to column support, the wrapped configuration depicted provides a compact and streamlined technique for packaging the balloon 52 in its deflated state.

Typically, the balloon will be distributed in the wrapped configuration and it will not be unwrapped until inflated within the region of stenosis. The lumen created by wrapping the balloon is of sufficient size to permit desired movement and rotation of the guidewire within the wrapped balloon. Of course, depending upon the column support desired for this portion of the catheter, the balloon may be wrapped more tightly or loosely around the guidewire.

The wrapped configuration of the balloon typically is maintained by temporary bonds designed to tolerate the stresses applied to this portion of the catheter during introduction of the device across a region of stenosis, and yet release when the balloon is inflated. Such a bond may be achieved using any well-known technique, for example, adhesives or ultrasonic bonding. Because of the typically high inflation pressures employed for inflation of the balloon, there is a wide range of choice of temporary bonding techniques. In other embodiments of the invention, the balloon may be maintained in a wrapped position by a deformable stent or generally tube-shaped material. Once the balloon is introduced into the region of stenosis and inflated, the deformable stent can be deployed, maintaining the artery lumen open.

FIGS. 6F–6G illustrate a device similar to the one depicted in FIGS. 6D–6E. The segment 81 of the guidewire 80 within the wrapped balloon is lower in profile than the corresponding profile of the guidewire within the device depicted in FIGS. 6D–6E. Again, wrapping and reversible bonding of the balloon are used to confer column support to the balloon. FIG. 6F illustrates the device during inflation. FIG. 6G is a side view of the device in the wrapped deflated condition. Reducing the profile of the guidewire allows a lower crossing profile. Wrapping the balloon component around a low profile segment 81 of the guidewire also fixes the coaxial relationship of the catheter and guidewire. In this embodiment the balloon is wrapped in such a manner that the balloon folds 39 permit rotational movement of the wire, yet limit coaxial movement. This configuration permits the guidewire 80 to enhance the pushability of the entire system. In effect, the force required to advance the catheter within a lesion can be applied to the guidewire 80 and not to the catheter component. This allows the shaft of the device to have thinner walls than other prior art catheters allowing separation of the catheter from the guidewire. To facilitate withdrawal of the catheter from the guidewire, transition zones 155 connecting the low profile segment 81 to the balance of the guidewire are tapered, as shown in FIG. 6G.

FIGS. 7A–7F are side views of the distal aspects of a series of single-channel, self-vented fixed-wire or semi-movable dilatation balloon catheter-guidewire systems. Semi-movable catheter systems permit limited coaxial catheter-guidewire inter-component mobility whereas fixed-wire systems provide no corresponding coaxial inter-component mobility. The distal catheter embodiments illustrated in FIGS. 7A–7F all permit limited coaxial and infinite rotational mobility of the guidewire components relative to the catheter components of these systems. Therefore, these embodiments can be used in the construction of either semi-movable or fixed-wire dilatation balloon devices. For these systems, it is the configuration of the respective proximal adapters (not shown) that define the coaxial mobility of the components and therefore their functional class. Below we discuss the application of these embodiments to the construction of semi-movable dilatation balloon systems but with the understanding that these designs have application to the construction of fixed-wire systems as well. (See FIG. 9B).

The features that distinguish these systems from the previous include: (1) the crossing profile, (2) the configuration of the guidewire components, and (3) the permanence of the guidewire components. These systems have lower crossing profiles than the systems described previously. The guidewires contained in these systems are non-uniform in profile and cannot be separated from the catheter components. The use of these systems obligates the operator to sacrifice intraluminal access in the event that an exchange procedure is required.

To our knowledge all prior art semi-movable dilatation balloon catheter systems contain multi-lumen catheter shafts. The use of our seal eliminates the need to separate the guidewire channel from the hydraulic channel in the construction of these devices. The use of our seal thus makes possible the construction of a variety of hydraulically competent, single-channel, self-vented semi-movable systems that provide a superior combination of proximal shaft profile, pushability, hydraulic performance, steerability and trackability relative to the semi-movable systems of the prior art.

FIG. 7A is a reference diagram expanded in FIGS. 7D–7F to depict more clearly the corresponding regions of the catheter.

FIG. 7B is an enlarged view of the transition zone 88 between the proximal end 87 of the guidewire tip-coils 152 and the distal end 76 of the catheter component of each system illustrated in FIGS. 7A, 7C–7F. The distal aspect 76 of the catheter, composed of a segment of polyimide tubing 71 bonded to the luminal surface of the balloon 52, is constructed with outside dimensions that approximate the corresponding dimensions of the guidewire tip coil 152. This relationship provides a smooth surface transition between the guidewire and the catheter and allows infinite inter-component rotational mobility.

FIG. 7C illustrates the coaxial mobility of the guidewire of the device depicted in FIG. 7A. In general, for a conventional length semi-movable angioplasty catheter, the guidewire can be advanced a distance 96 of approximately 30cm with respect to the corresponding catheter component. Advancement of the guidewire this distance brings the proximal end of tubular element 71 in juxtaposition with a taper 155 in guidewire 80. (See FIG. 8B.) The enlarged portion of taper 155 cannot be accommodated within the tubular element 71, thus limiting the coaxial mobility of the guidewire 80. The length 96 thus can be adjusted by placing the taper 155 proximally or distally along the length of the guidewire mandrel 150 during construction of this component.

FIG. 7D is an enlarged view of the distal aspect of the device depicted in FIGS. 7A–7C. For this device, the polyimide tubing 71 is bonded proximally to shaft tubing 66 and distally to the luminal surface of balloon 52. Tubing 71 provides column support to the balloon 52 and limits the torsion that can be applied to the balloon component during guidewire rotation. In one embodiment, the polyimide tubular element 71 is glued to a region of the luminal surface of the shaft tubing 66 and to the distal tip of the balloon. Given the length-to-width ratio of semi-movable devices, the use of off-center bonds to join tubular elements 66 and 71 does not compromise the functional characteristics of the device and simplifies construction. Alternatively, a spacer 72 can be installed within this joint to align the tubular elements 66, 71 as illustrated in FIG. 7D. FIG. 7D further illustrates the spatial relationship of the radiopaque balloon marker 86 to the tubular element 71.

FIG. 7E illustrates another embodiment of the distal aspect of a semi-movable device. This embodiment further can be adapted to the construction of a fixed-wire device as shown in its entirety in FIG. 10B. The central tubular element 71 of this device includes a fenestration 73 that allows air to escape from the hydraulic channel and the balloon. The device illustrated in FIG. 7F is similar to the device depicted in FIG. 7E, but the central tubular element 71 in FIG. 7F can rotate about the axis of the catheter. Thus the guidewire can rotate easier than absent the tubing.

FIG. 8 illustrates full length side views of the preferred embodiment of a semi-movable device of our invention. FIG. 8A illustrates the appearance of this device with the guidewire 80 in the retracted condition, while FIG. 8B illustrates the appearance of the device with the guidewire in the advanced condition. The device consists of a proximal adapter 202, shaft 66, balloon component 52, inner member 71, guidewire 80 and guidewire rotator 222. The device contains a seal 1 at the distal catheter-guidewire interface. The proximal adapter 222 consists of a housing 204, hydraulic side arm 32, and an adjustable liquid-tight sealing means that accommodates a movable guidewire. The adjustable sealing means consists of an O-ring 139, housing 204 and rotator 201. The interface 207 between the housing 204 and the rotator 201 is threaded. Clockwise rotation of the rotator 201 relative to the housing 204 tightens the seal created by the O-ring and guidewire. Continued clockwise rotation ultimately seizes the guidewire to the housing. Counter-clockwise rotation of rotator 201 relative to housing 204 releases the housing from the guidewire and thereby permits coaxial movement of the guidewire through the housing. Continued counter-clockwise rotation eventually opens the seal created by the O-ring 139 and guidewire 80. The proximal adapter 202 contains a single channel 64 that communicates with channel 34 of side arm 32. The distal end 37 of side arm 32 couples with a Luer-locking adapter. The catheter itself consists of a shaft 66, strain release 200, inner member 71, balloon component 52, and radiopaque marker band 86. The single-channel shaft 66 includes a relatively rigid proximal tubular segment 35 and a relatively flexible distal tubular segment 36. This shaft construction enables manufacture of the device with an optimal combination of proximal pushability and distal flexibility. Polyimide typically forms the shaft tubular element 35. Tubular element 36 is joined at joint 72 by an adhesive bond to polyimide tubing 71 extending through the balloon 52. Tubular element 71 contains a fenestration 73, within the distal confines of the balloon 52, that functions to vent air from the confines of the hydraulic channel 64 of the device. The guidewire 80 consists of a progressively tapered mandrel 150, tip coil 152 and shaping ribbon (not shown). The tip coils 152 are secured to the mandrel 150 by the shaping ribbon 162 (see FIG. 12E) and solder joint 174. The guidewire rotator 222 includes two rotatable elements 220, 226 and pin-vise 224. The interface between elements 220 and 226 describes a right-hand screw.

The device illustrated in FIGS. 8A–8B is fully vented, hydraulically competent, single channel and provides infinite guidewire rotational mobility and limited coaxial guidewire mobility. As shown in FIG. 8B, the guidewire 80 can be advanced a distance 96 relative to the catheter component, which corresponds to the distance separating the proximal end of tubular element 71 from the guidewire taper 155 when the guidewire is fully retracted. For catheters of conventional length, this distance typically equals approximately 30cm.

FIGS. 9A–9E illustrate the distal region of each one of a series of low-profile, single-channel, vented, fixed-wire devices that contain infinitely rotatable guidewires. In contrast to the embodiments depicted in FIGS. 7A–7F, the embodiments illustrated in FIGS. 9A–9E do not permit coaxial catheter-guidewire intercomponent mobility. Therefore these structures are more applicable to fixed-wire devices, than to semi-movable devices.

In contrast to the devices depicted in FIGS. 7A–8B that rely upon the catheter shafts 66 to provide column support for the balloon component via tubular elements 71 and joints 72, the devices depicted in FIGS. 9B–9E rely upon the use of chips 91, secured to guidewire 80, to provide column support for tubular elements 71 and thus balloon components 52. These chips 91 comprise opaque materials such as gold or platinum, and by that provide a marker for the location of the balloon, i.e., a radiopaque marker chip. Alternatively, these chips might comprise a segment of radiolucent tubing. For the devices illustrated in FIGS. 9A–9E two chips 86, 91 are shown; the former being radiopaque and the latter being radiolucent. Only one chip is needed when chip 91 employs radiopaque material.

Figure 9:
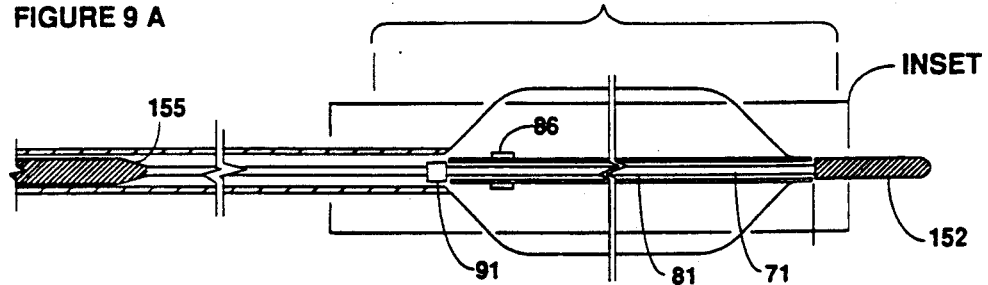
FIGS. 9A-9E illustrate distal portions of a series of fixed-wire dilatation balloon catheter/guidewire systems.
Figure 9:
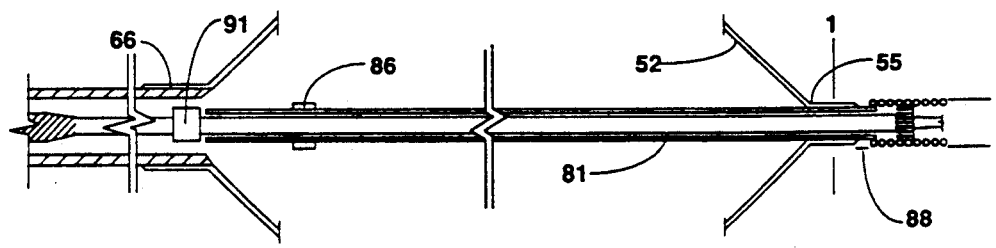
Figure 9:
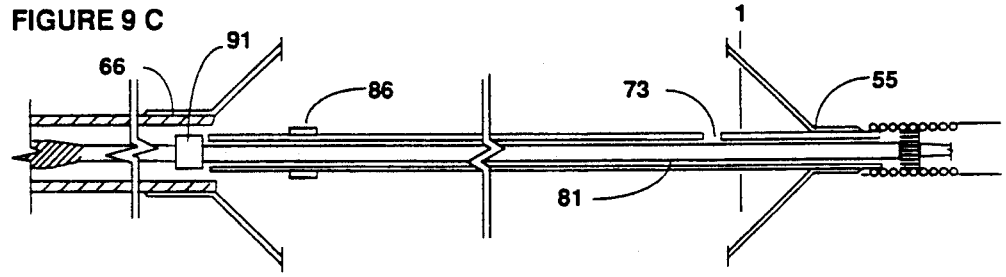
Figure 9:
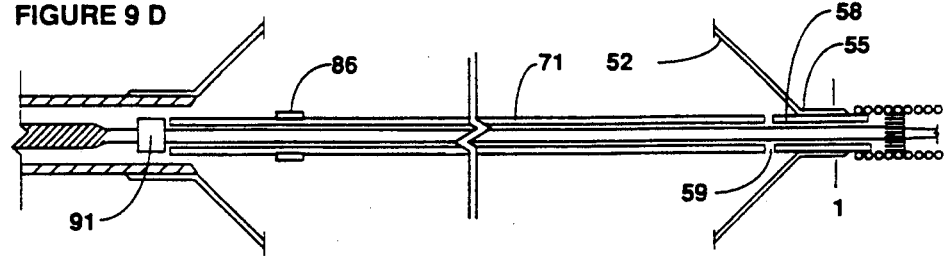
Figure 9:
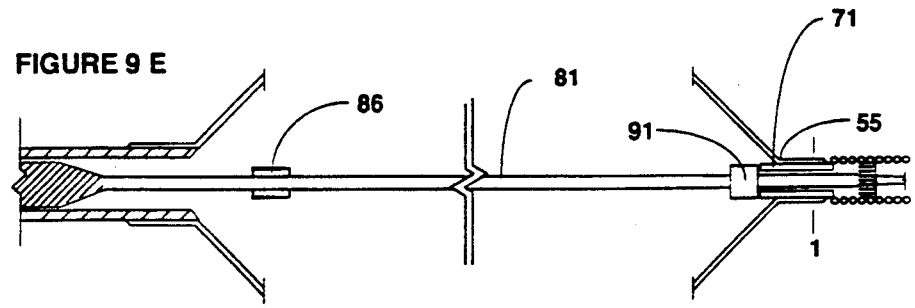

FIG. 9A is a diagram that contains an inset expanded in FIGS. 9B–9F to illustrate a corresponding region of the catheter.

FIG. 9B is a side view of the distal aspect 50 of the device pictured in FIG. 9A. The device depicted in FIG. 9C is similar to the device depicted in FIG. 9B, but the tubular element 71 includes a fenestration 73 to vent air from the balloon. The device depicted in FIG. 9D is similar to the device depicted in FIG. 9C, but the tubular element 71 is free to rotate within the balloon 52. Thus, the guidewire can rotate easier than absent the tubing. FIG. 9E illustrates a fixed-wire system similar to the system depicted in FIG. 9C, but tubular element 71 is shorter. Again, chip 91 affords column support for the balloon and a radiopaque material can be used in the manufacture of this chip. This approach allows manufacture of a device of lower crossing profile having a more flexible deflated balloon than the devices in FIGS. 9B–9D because tubular element 71 does not contribute to the rigidity or profile of the balloon component of this system.

Figure 10:
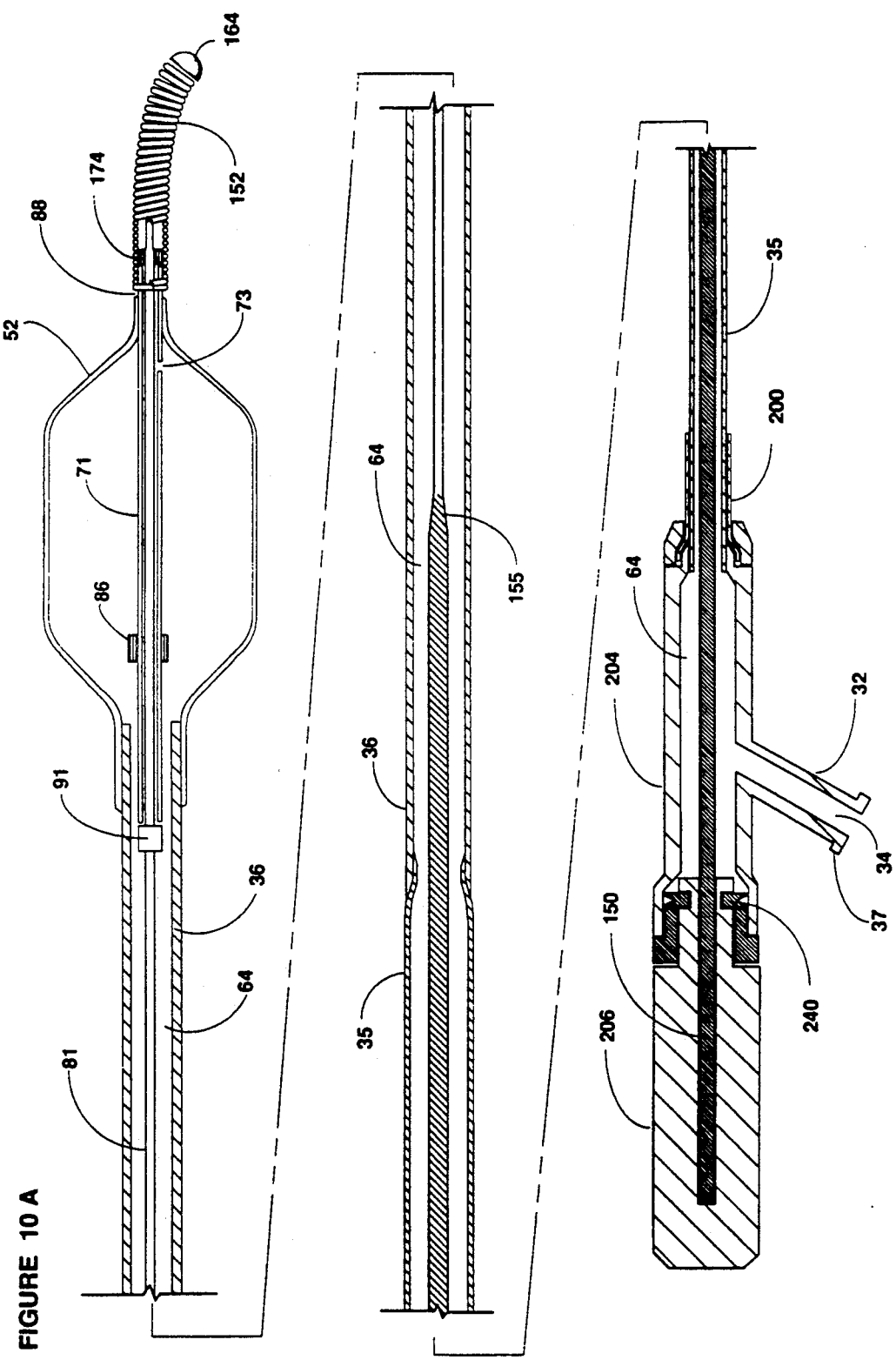
FIGS. 10A-10B illustrate detailed full length views of fixed-wire dilatation balloon catheter/guidewire systems.
Figure 10:
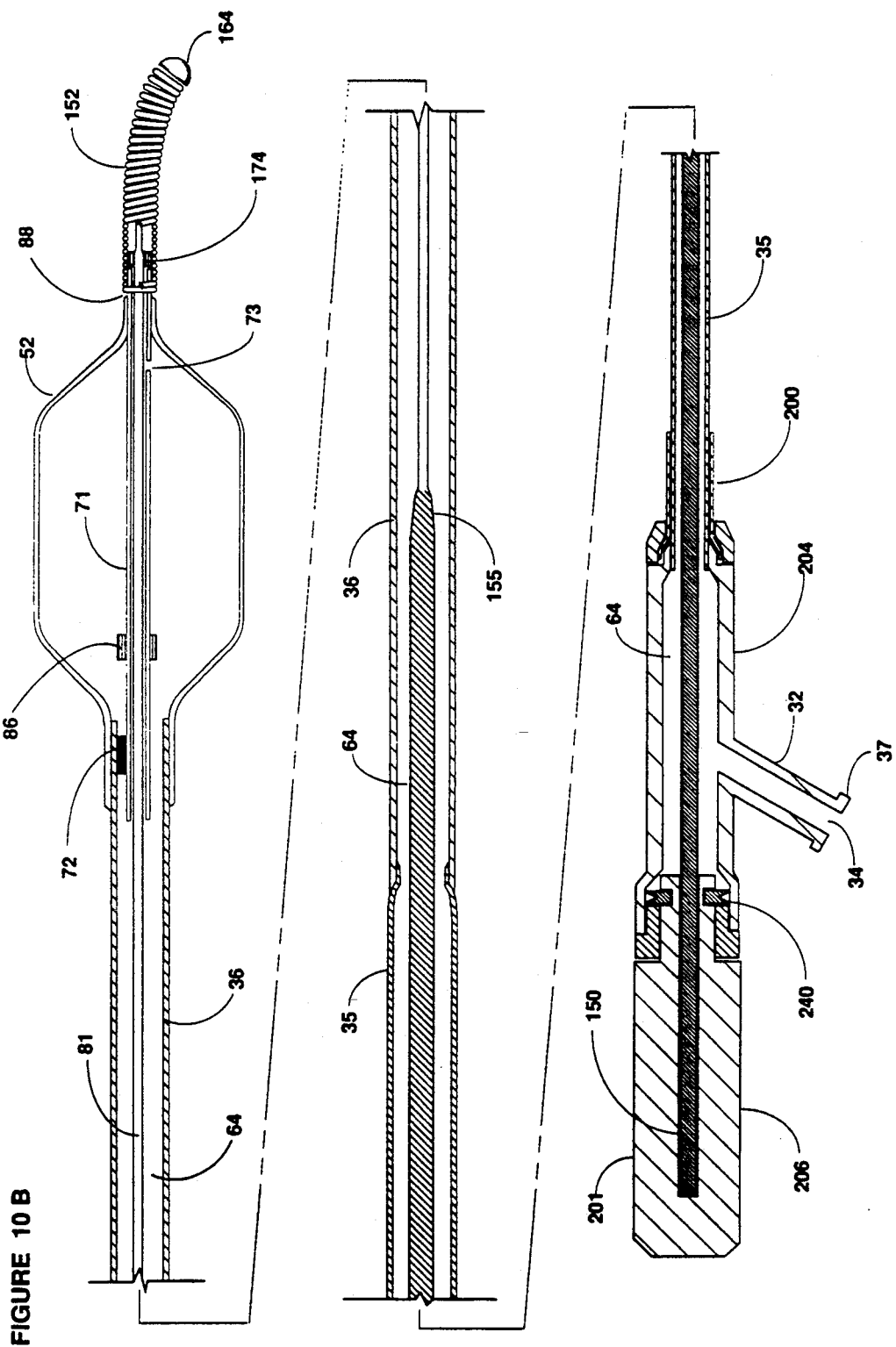

FIGS. 10A–10B are full length side views of two different configurations of fixed-wire dilatation balloon catheters. These two designs differ with respect to the means by which column support is provided to the balloon 52. For the device illustrated in FIG. 10A, a chip 91 provides column support for tubular element 71 and balloon component 52. This configuration corresponds to the design illustrated in FIG. 9C. For the device illustrated in FIG. 10B, an adhesive joint 72 joins shaft element 36 to inner member element 71 to provide column support to the balloon 52. This configuration corresponds to the approach illustrated in FIG. 7E. These devices thus provide a proximal adapter, single lumen catheter shaft 35, 36, dilatation balloon 52, vent 73 and a guidewire 80 of non-uniform profile this is free to rotate within the confines of the system. The proximal adapters comprise a single lumen housing 204, O-ring 240, side arm 32 and rotator 206. The side arms 32 contain a channel 34 that communications with the hydraulic lumen 64 of the device and couples to a Luer-locking adapter. The catheter shafts include a strain relief device 200, relatively rigid proximal shaft tubular element 35, and relatively flexible distal shaft tubular element 36. The guidewire 80 comprises a tapered mandrel 150 and tip coil 152. The tip coil 152 is soldered to the respective mandrel 150 by joints 164,174 and shaping ribbons (not shown). The composite designs illustrated in FIGS. 10A and 10B provide functionally comparable, hydraulically competent, self-vented, low profile, single-channel fixed-wire dilatation balloon catheters that provide infinite catheter/guidewire intercomponent rotational mobility, but no corresponding coaxial mobility.

Figure 11:
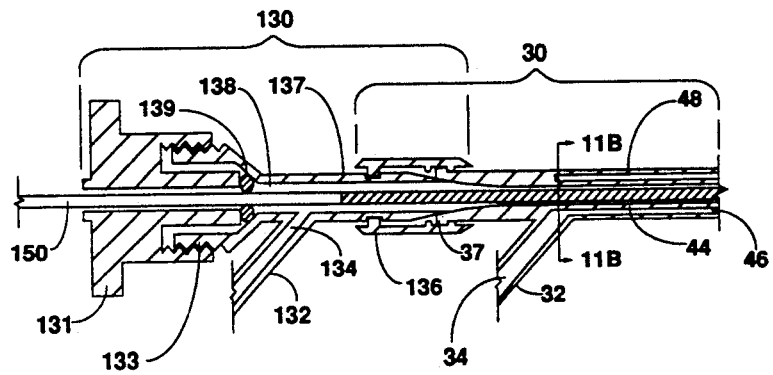
FIGS. 11A-11B are side and end views of the proximal portion of a conventional prior art multi-channel dilatation balloon catheter coupled to a conventional prior art Y-adapter.
FIGS. 11C, 11E-11H illustrate proximal portions of catheters employing our seal.
FIG. 11D is a side view of a Y-adapter that employs our seal.
Figure 11:
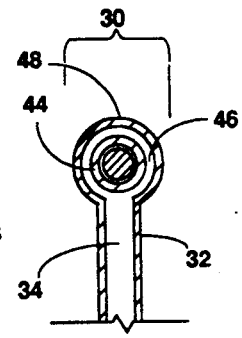
Figure 11:
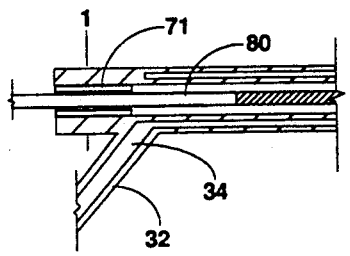
Figure 11:
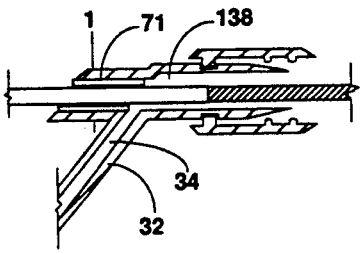
Figure 11:
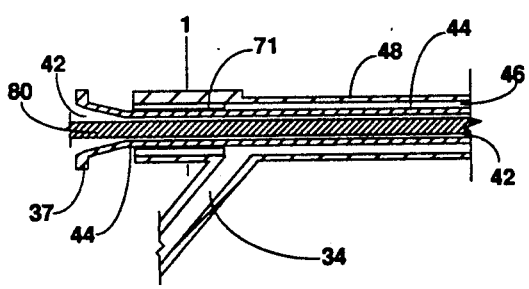
Figure 11:
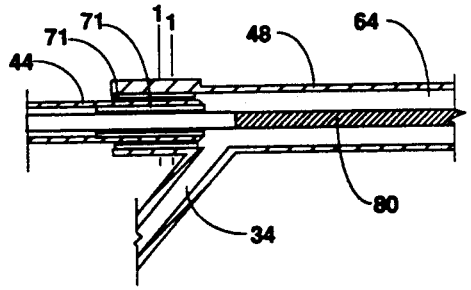
Figure 11:
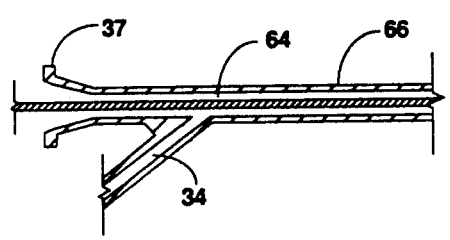
Figure 11:
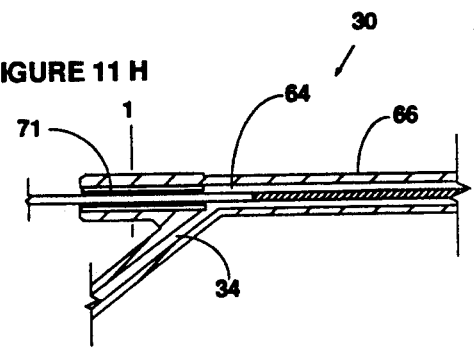

FIG. 11A is a side view of a proximal segment 30 of a prior art coaxial dilatation balloon catheter coupled, by a Luer-Lock fitting 37, 136, to a prior art Y-adapter 130. The Y-adapter 130 contains an O-ring 139 between two independently movable structures 131, 137. The ring prevents blood loss from the guidewire channel 42. Clockwise rotation of the proximal component of the device 131 compresses the O-ring 139, which in turn creates a seal between the adapter and the guidewire 80. The Y-adapter derives its name from the perfusion port 134 that connects at an oblique angle.

Significant functional limitations are inherent to Y-adapters of the prior art. The 0-ring valve 139 usually requires constant adjustment, a significant distraction for the operator. In addition, chamber 138 adjacent the 0-ring valve 139, often collects blood clots because it cannot be flushed with fluid introduced into the device via flush port 134. FIG. 11D illustrates the use of our seal in the construction of a Y-adapter. The central lumen 138 of this device does not contain a blind lumen to collect embolic material.

FIG. 11C illustrates the proximal aspect 30 of a dual channel catheter that contains a seal of our invention between the luminal surface of the catheter and the surface of the guidewire 80. This seal eliminates the need for a conventional Y-adapter at the proximal catheter-guidewire interface and provides independent movement of the guidewire therethrough.

FIGS. 11E-11H illustrate the design of the proximal aspect 50 of the device illustrated in FIGS. 6A-6C. The structure illustrated in FIGS. 11E-11H permits withdrawal of the central element beyond the level of the flush channel 134. The seal between tubular element 48 and the guidewire 80 has two coaxial interfaces as shown in FIG. 11F. The first interface is disposed between the two tubular elements that comprise the catheter shaft 44, 48. The second is disposed between the central tubular element 44 and the guidewire 80.

FIGS. 11G-11H illustrate the proximal aspects 30 of single-channel over-the-wire devices of our invention. FIG. 11G illustrates a device constructed with a Luer-Locking fitting 37 at the distal end, which can be coupled to a conventional or modified Y-adapter. FIG. 11H illustrates the use of our seal 1 in the construction of the proximal aspect 30 of single channel over-the-wire catheters. This approach circumvents the need to employ a Y-adapter.

FIGS. 12A-12E illustrate a series of guidewire configurations that can be used with the devices described herein. The wires illustrated in FIGS. 12A-12C are intended for use with over-the-wire systems. The wires illustrated in FIGS. 12D and 12E are intended for use in semi-movable and fixed-wire systems. FIG. 12E is an enlarged phantom view of the wire contained within the inset of FIG. 12D.

FIGS. 12A-12C illustrate guidewires that contain segments 81 with smooth surfaces. FIG. 12A illustrates the use of a segment of polyimide tubing 71, bonded to the surface of a guidewire of conventional design, to provide a region 81 with a smooth surface. In FIG. 12A, the guidewire has a progressively tapered core 150 with a coiled outer layer 152 bonded to the core by suitable means 170.

FIG. 12B illustrates the use of a length of polyimide tubing 71, installed over a region of wire coil 167 of relatively reduced profile, to permit the construction of a guidewire of uniform surface dimensions, that contains a smooth segment 81. FIG. 12C illustrates the use of a length of polyimide tubing 71, installed over a flexible elastic material 158 to provide a guidewire of uniform dimensions having a smooth segment 81. The embodiments depicted in FIGS. 12A and 12B are particularly beneficial when enhanced rigidity is desirable. The extent to which the polyimide tubing 71 affects the rigidity of the composite segment can be modified by changing the wall thickness of the polyimide tubing used in the inner member of the interface; however, this approach does not permit a composite segment to have flexibility commensurate with the adjacent components of the wire. Alternatively, the polyimide can be applied directly over an elastic material 158 to diminish the rigidity of the composite structure. (See FIG. 12C.) This approach gives the smooth component of the guidewire enhanced flexibility compared to the previous embodiments. With the proper combination of materials, this configuration provides a guidewire with relatively uniform flexibility throughout its length. Alternatively, precision co-extrusion over a preformed tapered mandrel can be used to manufacture guidewires and segments of guidewires with smooth surfaces. Although these figures and text review various methods to construct segments of wires with smooth surfaces, this review is not intended to be exhaustive. Our seal will function with any guidewire of any configuration that provides a surface that conforms to the luminal surface of the sleeve component 7 of the catheter.

FIG. 12D is an side view of the distal aspect of the guidewire contained within semi-movable and fixed-wire devices that employ our seal. FIG. 12E is an enlarged phantom profile view of the guidewire component contained within the inset of FIG. 12D. This wire contains a mandrel 150 that is continuous with a progressively tapered core element 157. A flexible wire coil 152 is attached to the core element 157 by a solder joint 174, a thin shaping ribbon 162 and solder joint 164. This configuration provides a guidewire with segments of progressively increasing flexibility. In one embodiment, the proximal aspect 87 of the wire coil 152 is tapered outward to accommodate the tip of the catheter 76 movably disposed on the core element 157. The insertion of the catheter tip 76 within the confines of the guidewire coil 152 enhances the structural integrity of this relatively delicate region of the catheter and provides a smooth transition zone 88 between the guidewire and the catheter. In the preferred embodiment, the junction of the guidewire and catheter permits full rotational and coaxial movement. The insertion of a rotationally disposed catheter tip 76 within the guidewire coil 152 is a significant departure from conventional structures.

FIGS. 13A-13K illustrate balloon-on-a-wire systems employing our invention. A balloon-on-a-wire system, as the name implies, refers to a guidewire 151 containing a lumen 190 that communicates with a balloon 52 disposed thereon. Although prior art balloon-on-a-wire systems exist, these systems have balloons 52 that are immovably bonded to the guidewire. Such prior art configurations are subject to the limitations of fixed-wire systems that contain adhesive bonds at the distal catheter-guidewire interface. Our seal enables the manufacture of self-vented, single-channel balloon-on-a-wire systems containing balloon components that are rotatably disposed on the guidewire components. These systems provide superior guidewire-mediated rotational torque transmission and therefore superior steerability compared to the prior art. In addition, these systems are less prone to balloon wrapping and guidewire fracture than the prior art. In short, the use of our seal enables the construction of single channel, self-vented balloon-on-a-wire devices that provide a superior combination of shaft profile, hydraulic performance, steerability and structural integrity than prior art devices.

As shown in FIGS. 13A-13C and 13D-13F, the balloon-a-wire system of our invention has a guidewire extending the length of the system, with a balloon-catheter shaft unit 175 that can rotate thereon. The guidewire has several components bonded together to form a single unit. These components include a hub 148, shaft 151, core element 154, flexible coil 152, and coil tip 164. The shaft 151 of the device consists of stainless steel hypo-tubing welded to the core element in region 153. A solder joint 174 connects the core element 154 to the flexible tip coil 152 (see FIG. 13G).

The balloon-catheter shaft unit 175 has a balloon 52 and two segments of polyimide tubing 71, 166 bonded together at location 172 to form a single unit. Polyimide is used in the construction of the distal catheter shaft 166 because it is more resilient than stainless steel. It will accept bending more readily, without sustaining kinks, than stainless steel. Therefore, it is more suitable for use in the construction of this component of the shaft, which must be capable of traversing tortuous blood vessels. The proximal and distal ends of this balloon-catheter shaft unit 175 employ seals 1 of our invention with the corresponding elements of the guidewire. These seals permit the balloon-catheter shaft unit 175 to rotate about the axis of the guidewire, with preserved hydraulic competence. The use of these seals in this device further provides a means of venting air from the hydraulic channels, enhancing the safety of these systems and expediting the process of preparing these systems with contrast.

FIGS. 13A-13C illustrate one embodiment of our balloon-on-a-wire device in which all the components are coaxial in disposition. Alternatively, our device can be constructed with components that are not coaxial, as illustrated in FIGS. 13D-13F. For this latter design, the guidewire core element 154 is bonded directly onto the lumenal surface of the hypo-tubing 151 that comprises the shaft of the device. Similarly, the outer surface of member 71 is bonded directly onto the luminal surface of the polyimide tubing 166. Given the length-to-width ratio of balloon-on-a-wire devices, the use of off-center bonds does not compromise the functional characteristics of the device and further simplifies the process of catheter construction. FIGS. 13G-13J includes an enlarged, detailed, foreshortened view and a series of cross-sectional views of the device depicted in FIG. 13A.

FIG. 13K illustrates an alternative embodiment of the device depicted in FIGS. 13A-13C and 13D-13F. In this device, a radiopaque marker chip 91, typically gold or platinum, provides a marker for the balloon, which combined with tube 71 provides column support for the balloon.

FIGS. 14A-14G are schematic representations of complete balloon angioplasty systems to illustrate that our seals enable the construction of composite dilatation balloon catheter systems with fewer channels and lower shaft profiles than previously possible. The catheter components are shown straight for comparison. FIGS. 14A, typical of the prior art and described further below, includes a guiding catheter 210, dilatation balloon catheter, guidewire 80 and supportive apparatus. FIGS. 14B-14G are similar representations of a substantially lower profile composite system of our invention that contains multiple seals 1 disposed between a variety of independently movable surfaces. The use of our seal enables dilatation systems containing multi-purpose hydraulic channels. The system illustrated in FIGS. 14B-14E illustrates advantages inherent in the use of our seals in the construction of composite catheter systems. FIGS. 14B-14E illustrate that seals of our invention are particularly applicable to composite catheter systems containing a variety of devices, such as dilatation balloon/laser systems, dilatation balloon/atherectomy systems, dilatation balloon/intravascular ultrasound systems, independent atherectomy systems, etc., that require the transmission of hydraulic pressure or the conveyance of fluid within the device.

FIG. 14A is a side view of a complete prior art catheter system used to perform an angioplasty. The dilatation balloon catheter, prepared with a guidewire 80, is introduced into the coronary vasculature via the lumen 215 of guiding catheter 210. The lumen 215 of guiding catheter 210 is coupled to a three-way manifold 270 and a syringe 280 by a. Y-adapter 130 and a perfusion channel 260. The guidewire lumen 42 of the dilatation catheter is coupled similarly via a Y-adapter 130 to a three-way manifold 270 and a corresponding injection syringe 284. The hydraulic channel 46 of the dilatation catheter is coupled directly to an inflation syringe 282. The composite structure contains three concentric tubes 44, 48, 210 and three independent lumens 42, 44, 215 at the level of introduction through the skin 300. (See FIG. 14B.) The application of pressure to the syringe 280 injects contrast into the vasculature distal to the guiding catheter and enables performance of an intra-operative angiogram. Application of pressure to syringe 282 transmits hydraulic pressure along the length of the dilatation catheter to inflate the balloon. The application of pressure to syringe 284 introduces contrast via the guidewire channel 42 of the balloon catheter and allows performance of selective angiography of the vessel containing the balloon catheter. The three-way manifolds 270 communicate variously with pressure transducers, flush ports and contrast reservoirs and permit intra-operative assessment of the patient's hemodynamic status. This system is bulky and contains considerable duplication of effort.

FIG. 14G is an off-center profile view of a vented ultralow profile single-channel dilatation balloon catheter system of our invention. It contains a prewrapped/reversibly bonded dilatation balloon 52, a distal catheter shaft 66 of precise and uniform dimensions, a fenestrated proximal catheter shaft 110, and a guidewire 80 of non-uniform profile. FIGS. 14C-14E illustrate the use of the previous dilatation catheter system with one embodiment of a very low profile guiding catheter 216 of our invention.

FIG. 14C is a profile view of a guiding catheter 216 containing a polyimide sleeve 71 that precisely fits the outside dimensions of the catheter shaft 66. The lumen of this guiding catheter communicates with a three-way adapter 270 and multi-purpose injection syringe 286.

FIG. 14D illustrates the appearance of the overall system following introduction of the dilatation catheter system. The shaft of the dilatation catheter forms a seal with the two polyimide sleeves disposed within the proximal and mid-portions of the guiding catheter lumen 218. The fenestrations in the dilatation catheter shaft 110 permit direct communication between the multi-purpose perfusion channel 266 and the multi-purpose hydraulic channel 64 of the dilatation catheter.

FIGS. 14C-14E illustrate that this system can be used to perform coronary arteriography (FIG. 14C); perform selective coronary arteriography (FIG. 14D); and transmit hydraulic pressure (FIGS. 14E) depending upon the presence or absence of the dilatation system within the channel of the guiding catheter and depending upon the location of the guidewire relative to the dilatation system. This system permits the performance of all three of these functions with a particularly low-profile device. Additionally, the hydraulic pressure is conducted largely by the lumen 218 of the guiding catheter 216. Given the relationship between hydraulic performance and hydraulic channel dimensions, this system permits the construction of a high performance, highly steerable, ultra-low profile telescoping angioplasty system.

Although many embodiments of the invention have been described and discussed above, it will be apparent to those of skill in the art that by employing our invention, variations may be made in these embodiments to achieve other catheter designs having beneficial features. The scope of our invention may be determined from the following claims.

What is claimed is:

1. A single-channel dilatation balloon catheter/guidewire system, the catheter of which is semi-movable relative to the guidewire, said system comprising:

a tubular catheter shaft having a balloon secured to the distal end thereof and an opening at the distal end of said balloon;

a length of non-axially-collapsible inner tubing positioned inside said balloon, the distal end of said inner tubing secured to the distal end of said balloon in a manner preventing fluid passage through said opening other than through said inner tubing, the proximal end of said inner tubing secured to said tubular catheter shaft at or adjacent to the proximal end of said balloon in a manner permitting fluid passage between said tubular catheter shaft and the interior of said balloon, said inner tubing thereby providing axial support to said balloon while permitting inflation and deflation thereof from said tubular catheter shaft; and a guidewire extending through said tubular catheter shaft and said inner tubing and terminating in a tip extending distal to said opening, said guidewire further containing a constant diameter segment immediately proximal to said tip, exceeding said inner tubing in length, passing through said inner tubing and axially movable relative thereto between a retracted position and an extended position while still spanning the full length of said inner tubing said guidewire joined neither to said tubular catheter shaft, said inner tubing nor said balloon, and thereby free to rotate to an unlimited degree relative to said tubular catheter shaft, said inner tubing and said balloon; and said inner tubing and said constant diameter segment of said guidewire, at all relative positions between said retracted position and said extended position, defining an annular space sufficiently narrow to prevent the passage of a liquid having a viscosity at least as great as that of water during inflation of said balloon with said liquid.

2. A single-channel dilation catheter/guidewire system in accordance with claim 1 in which said tubular catheter shaft is comprised of a proximal segment and a distal segment, said distal segment being of greater flexibility relative to said proximal segment, and said proximal end of said inner tubing is secured to said distal segment adjacent to the proximal end of said balloon.

3. A single-channel dilatation catheter/guidewire system in accordance with claim 1 in which:

said constant diameter segment of said guidewire is a segment of lesser diameter than that of a larger diameter segment proximal thereto, whereby when said guidewire is in said extended position, said larger diameter segment of said guidewire abuts said proximal end of said inner tubing, and said tip of said guidewire has a diameter exceeding that of said opening, whereby when said guidewire is in said retracted position, said tip abuts said opening.

4. A single-channel dilatation catheter/guidewire system in accordance with claim 1 which said inner tubing contains a fenestration communicating the interior of said balloon with said annular space, thereby permitting escape of air from said balloon and other regions of said catheter into said annular space and out said opening at the distal end of said balloon during charging of said catheter with liquid.

5. A single-channel dilatation catheter/guidewire system in accordance with claim 1 in which said constant diameter segment of said guidewire has a diameter of from about 0.005 inch to about 0.010 inch, and said annular space has a width of from about 0.00025 inch to about 0.0025 inch.

6. A single-channel dilation catheter/guidewire system in accordance with claim 1 in which said annular space is filled with a solid or semi-solid lubricant.

* * * * *